US011015202B2

United States Patent
Ishii et al.

(10) Patent No.: US 11,015,202 B2
(45) Date of Patent: May 25, 2021

(54) COMPLEX CONTAINING OLIGONUCLEOTIDE HAVING IMMUNOPOTENTIATING ACTIVITY AND USE THEREOF

(71) Applicants: NATIONAL INSTITUTES OF BIOMEDICAL INNOVATION, HEALTH AND NUTRITION, Ibaraki (JP); DAIICHI SANKYO COMPANY, LIMITED, Tokyo (JP)

(72) Inventors: Ken Ishii, Ibaraki (JP); Kouji Kobiyama, Ibaraki (JP); Taiki Aoshi, Ibaraki (JP); Fumihiko Takeshita, Tokyo (JP); Yuji Kasuya, Tokyo (JP); Takako Niwa, Tokyo (JP); Makoto Koizumi, Tokyo (JP)

(73) Assignees: NATIONAL INSTITUTES OF BIOMEDICAL INNOVATION, HEALTH AND NUTRITION, Ibaraki (JP); DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/227,902

(22) Filed: Dec. 20, 2018

(65) Prior Publication Data
US 2019/0112606 A1 Apr. 18, 2019

Related U.S. Application Data

(63) Continuation of application No. 15/022,856, filed as application No. PCT/JP2014/074835 on Sep. 19, 2014, now Pat. No. 10,202,606.

(30) Foreign Application Priority Data

Sep. 20, 2013 (JP) .................. 2013-196206

(51) Int. Cl.
| | | |
|---|---|---|
| *C12N 15/117* | (2010.01) | |
| *A61K 39/39* | (2006.01) | |
| *A61K 31/7125* | (2006.01) | |
| *A61K 31/713* | (2006.01) | |
| *C07H 21/04* | (2006.01) | |
| *A61K 39/145* | (2006.01) | |
| *A61K 39/155* | (2006.01) | |
| *A61K 39/12* | (2006.01) | |
| *C08B 37/00* | (2006.01) | |
| *C12N 7/00* | (2006.01) | |
| *A61K 39/00* | (2006.01) | |

(52) U.S. Cl.
CPC .......... *C12N 15/117* (2013.01); *A61K 31/713* (2013.01); *A61K 31/7125* (2013.01); *A61K 39/12* (2013.01); *A61K 39/145* (2013.01); *A61K 39/155* (2013.01); *A61K 39/39* (2013.01); *C07H 21/04* (2013.01); *C08B 37/0024* (2013.01); *C12N 7/00* (2013.01); *A61K 2039/5252* (2013.01); *A61K 2039/55561* (2013.01); *A61K 2039/55583* (2013.01); *C12N 2310/17* (2013.01); *C12N 2310/315* (2013.01); *C12N 2310/351* (2013.01); *C12N 2310/3519* (2013.01); *C12N 2320/31* (2013.01); *C12N 2760/16134* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 7,521,433 B2 | 4/2009 | Kimura et al. | |
| 7,790,189 B2 | 9/2010 | Mizu et al. | |
| 8,017,742 B2 | 9/2011 | Sakurai et al. | |
| 2003/0026782 A1 | 2/2003 | Krieg | |
| 2003/0216346 A1 | 11/2003 | Sakurai et al. | |
| 2006/0084149 A1 | 4/2006 | Kimura et al. | |
| 2008/0262210 A1 | 10/2008 | Mizu et al. | |
| 2010/0143400 A1 | 6/2010 | Davis et al. | |
| 2011/0301230 A1 | 12/2011 | Sakurai et al. | |

FOREIGN PATENT DOCUMENTS

| | | |
|---|---|---|
| CN | 101745109 A | 6/2010 |
| CN | 102333538 A | 1/2012 |
| EP | 1142591 B1 | 4/2008 |
| EP | 1625850 B1 | 2/2012 |
| EP | 1369133 B1 | 8/2012 |
| JP | 2014-107272 A | 4/2004 |
| JP | 2006-069913 A | 3/2006 |
| JP | 2007-070307 A | 3/2007 |
| JP | 2008-100919 A | 5/2008 |
| JP | 2010-174107 A | 8/2010 |

(Continued)

OTHER PUBLICATIONS

Weiner (PNAS, 94:10833-10837, 1997).*

(Continued)

*Primary Examiner* — Patricia Duffy

(74) *Attorney, Agent, or Firm* — Leydig, Voit & Mayer, Ltd.

(57) ABSTRACT

The present invention provides an oligodeoxynucleotide containing humanized K type CpG oligodeoxynucleotide and poly deoxyadenylate, wherein the poly deoxyadenylate is placed on the 3'-side of the humanized K type CpG oligodeoxynucleotide. In addition, the present invention provides a complex containing the aforementioned oligodeoxynucleotide and β-1,3-glucan.

9 Claims, 33 Drawing Sheets

Specification includes a Sequence Listing.

(56) References Cited

FOREIGN PATENT DOCUMENTS

| | | |
|---|---|---|
| JP | 4878915 B2 | 2/2012 |
| WO | WO 2001/034207 A1 | 5/2001 |
| WO | WO 2002/072152 A1 | 9/2002 |
| WO | WO 2004/100965 A1 | 11/2004 |

OTHER PUBLICATIONS

Bohn et al., "(1→3)-β-D-Glucans as biological response modifiers: a review of structure-functional activity relationships," *Carbohydrate Polymers*, 28(1): 3-14 (1995).

Kobiyama et al., "K3-SPG is a novel nano-particulate CpG oligodeoxynucleotide complex with robust interferon induction and adjuvanticity," *Proceeding of the Japanese Society of Immunology*, 42: 163, abstract 2-I-W39-7-O/P (2013).

Kobiyama et al., "Nonagonistic Dectin-1 ligand transforms CpG into a multitask nanoparticulate TLR9 agonist," *Proc. Natl. Acad. Sci. U.S.A.*, 111(8): 3086-3091 (2014).

Koyama et al., "Plasmacytoid Dendritic Cells Delineate Immunogenicity of Influenza Vaccine Subtypes," *Science Translational Medicine*, 2(25): 25ra24 (2010).

Minari et al., "Enhanced Cytokine Secretion from Primary Macrophages due to Dectin-1 Mediated Uptake of CpG DNA/,β-1,3-Glucan Complex," *Bioconjugate Chemistry*, 22(1): 9-15 (2011).

Miyamoto et al., "Enhanced Immunostimulation with Crosslinked CpG-DNA/β-1,3-Glucan Nanoparticle through Hybridization," *Chemistry Letters*, 43(7): 991-993 (2014).

Miyamoto et al., "Selective Delivery of Oligonucleotide Using a β-1,3-glucan Receptor," *Cellulose Communications*, 19(1): 12-16 (2012).

Mochizuki et al., "Selective delivery of oligonucleotide using a β-1,3-glucan receptor," *Drug Delivery System*, 25(6): 565-572 (2010).

Mochizuki et al., "Dectin-1 targeting delivery of TNF-α antisense ODNs complexed with β-1,3-glucan protects mice from LPS-induced hepatitis," *J. Control. Release*, 151(2): 155-161 (2011).

Mochizuki et al., "Novel cancer vaccine using CpG-DNA/β-1,3-glucan complex," *Polymer Preprints, Japan*, 62(2): 4825-4826, item 1A11 (2013).

Shimada et al., "A Polysaccharide Carrier to Effectively Deliver Native Phosphodiester CpG DNA to Antigen-Presenting Cells," *Bioconjugate Chem.*, 18(4): 1280-1286 (2007).

Takeshita et al., "Cutting Edge: Role of Toll-Like Receptor 9 in CpG DNA-Induced Activation of Human Cells," *J. Immunol.*, 167(7): 3555-3558 (2001).

Temizoz et al., "Vaccine adjuvants as potential cancer immunotherapeutics," *Int Immunol.*, 28(7): 329-338 (2016).

Tougan et al., "TLR9 adjuvants enhance immunogenicity and protective efficacy of the SE36/AHG malaria vaccine in nonhuman primate models," *Hum. Vaccin. Immunother.*, 9(2): 283-290 (2013).

Japanese Patent Office, International Search Report in International Patent Application No. PCT/JP2014/074835 (dated Dec. 16, 2014).

Japanese Patent Office, Written Opinion in International Patent Application No. PCT/JP2014/074835 (dated Dec. 16, 2014).

Russian Patent Office, Office Action and Search Report in Russian Patent Application No. 2016115052 (dated Aug. 31, 2018).

Taiwanese Patent Office, Office Action in Taiwanese Patent Application No. 103132422 (dated Apr. 27, 2018).

\* cited by examiner

COMPLEX CONTAINING OLIGONUCLEOTIDE HAVING IMMUNOPOTENTIATING ACTIVITY AND USE THEREOF

CROSS-REFERENCE TO RELATED APPLICATIONS

This patent application is a continuation of copending U.S. patent application Ser. No. 15/022,856, filed on Mar. 17, 2016, which is the U.S. national phase of International Patent Application No. PCT/JP2014/074835, filed Sep. 19, 2014, which claims the benefit of Japanese Patent Application No. 2013-196206, filed on Sep. 20, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 2,802 bytesbytes ASCII (Text) file named "741312SequenceListing.txt," created Dec. 17, 2018.

TECHNICAL FIELD

The present invention relates to an oligonucleotide-containing complex having an immunostimulating activity, and use thereof. More particularly, the present invention relates to a complex comprising CpG oligodeoxynucleotide (ODN) having an immunostimulating activity, and β-glucan, and pharmaceutical use thereof.

BACKGROUND ART

CpG oligodeoxynucleotide (CpG ODN) is a short (around 20 base pair), single-stranded synthetic DNA fragment containing the immunostimulatory CpG motif, a potent agonist for Toll-like receptor 9 (TLR9), activates dendritic cells (DCs) and B cells to produce type I interferons (IFNs) and inflammatory cytokines (non-patent documents 1, 2), and acts as an adjuvant towards both Th1-type humoral and cellular immune responses including cytotoxic T-lymphocyte (CTL) responses (non-patent documents 3, 4). Therefore, CpG ODN has been postulated as a possible immunotherapeutic agent against infectious diseases, cancer, asthma, and pollinosis (non-patent documents 2, 5)

There are at least four types of CpG ODN, each of which has a different backbone, sequence, and immunostimulatory properties (non-patent document 6). D (also called A) type CpG ODN, typically comprise one palindromic CpG motif with a phosphodiester (PO) backbone and phosphorothioate (PS) poly G tail, that activates plasmacytoid DCs (pDCs) to produce a large amount of IFN-α, but fails to induce pDC maturation and B cell activation (non-patent documents 7, 8). The three other types of ODN consist of a PS backbone. K (also called B) type CpG ODN contains non-palindromic multiple CpG motifs, and strongly activates B cells to produce IL-6 and pDCs to maturation, but barely produce IFN-α (non-patent documents 8, 9). Recently, C and P type CpG ODN have been developed; these contain one and two palindromic CpG sequence(s), respectively, both of which can activate B cells like K type and pDCs like D type, although C type CpG ODN induces weaker IFN-α production compared with P type CpG ODN (non-patent document 10-12). Many superior K type CpG ODNs are described in patent document 1.

The D and P type CpG ODN have been shown to form high-order structures, Hoogsteen base-pairing to form parallel quadruplex structures called G-tetrads, and Watson-Crick base-pairing between cis- and trans-palindromic portions, respectively, that are required for robust IFN-α production by pDCs (non-patent documents 12-14). Although such higher-order structures appear necessary for localization to early endosomes and signaling via TLR9, they suffer from product polymorphisms, aggregation and precipitation, thereby hampering their clinical applications (non-patent document 15). Therefore, only K and C type CpG ODN are generally available as immunotherapeutic agents and vaccine adjuvants for human use (non-patent document 16 and 17). While K type CpG ODN enhances the immunogenicity of vaccines targeting infectious diseases and cancers in human clinical trials (non-patent documents 6, 16), chemical or physical conjugation between antigen and K type CpG ODN is necessary for the optimal adjuvant effects. These results indicate that these four (K, D, P, and C) types of CpG ODN have advantages and disadvantages, however the development of an 'all-in-one' CpG ODN activating both B cells and pDCs without aggregation is yet to be accomplished.

Schizophylan (SPG), a soluble β-1,3-glucan derived from *Schizophyllum commune*, is a drug approved in Japan as an enhancer of radiotherapy in cervical carcinoma patients, for the last three decades (non-patent document 18). Similarly, lentinan (LNT), a soluble β-1,3-glucan derived from shiitake mushroom, is a medicament approved in 1985, and used in combination with a fluoropyrimidine medicament for inoperable and recurrent gastric cancer patients (non-patent documents 19, 20). β-1,3-Glucan has been shown to form complex with poly deoxyadenylate (dA) as a triple helical structure (non-patent document 21).

Patent documents 2-4 disclose use of a water-soluble complex of β-1,3-glucan including schizophyllan and nucleic acid (gene), as a gene carrier. These documents describe that formation of the complex enhances an antisense action of the gene and a resistance action thereof against nuclease.

Patent document 5 discloses use of polysaccharides having a β-1,3-bond as a carrier (transfection agent) enhances the action of an immunostimulating oligonucleotide having a CpG sequence, wherein a phosphodiester bond is substituted by a phosphorothioate bond or phosphorodithioate bond.

Patent document 6 discloses an immunostimulating complex consisting of an immunostimulating oligonucleotide and β-1,3-glucan having a long β-1,6-glucosidebond side chain.

The present inventors previously demonstrated that mouse and humanized CpG ODN linked with poly dA having a phosphodiester bond at the 5' end complexed with SPG enhanced cytokine production and acted as an influenza vaccine adjuvant and a prophylactic or therapeutic agent for Th2 cell related diseases (non-patent documents 22, 23, patent document 7). When poly(dA) was added to the 5'-end of CpG of each of K type and D type to form a complex with SPG, the both showed enhanced activity while maintaining the property of K type and D type. However, it was difficult to achieve high yields of the CpG-SPG complex towards its more efficient and cost-effective preclinical as well as clinical development. Recently, when the poly(dA) having phosphorothioate bond linked to CpG ODN, the efficiency of complex formation was elevated by nearly 100% (non-patent document 24). However, a thorough investigation has not yet been conducted to identify the best humanized CpG sequence and optimization of factors to gain "all-in-one" activities of four types of CpG ODN.

Patent document 8 discloses a production method of an antigen/CpG oligonucleotide/β-1,3-glucan type ternary complex.

DOCUMENT LIST

Patent Documents patent document 1: U.S. Pat. No. 8,030,285 B2
patent document 2: WO 01/034207 A1
patent document 3: WO 02/072152 A1
patent document 4: JP-A-2004-107272
patent document 5: WO 2004/100965 A1
patent document 6: JP-A-2007-70307
patent document 7: JP-A-2008-100919
patent document 8: JP-A-2010-174107

Non-Patent Documents non-patent document 1: Hemmi, H., et al. A Toll-like receptor recognizes bacterial DNA. Nature 408, 740-745 (2000).
non-patent document 2: Krieg, A. M. Therapeutic potential of Toll-like receptor 9 activation. Nature reviews. Drug discovery 5, 471-484 (2006).
non-patent document 3: Brazolot Millan, C. L., Weeratna, R., Krieg, A. M., Siegrist, C. A. & Davis, H. L. CpG DNA can induce strong Th1 humoral and cell-mediated immune responses against hepatitis B surface antigen in young mice. Proceedings of the National Academy of Sciences of the United States of America 95, 15553-15558 (1998).
non-patent document 4: Chu, R. S., Targoni, O. S., Krieg, A. M., Lehmann, P. V. & Harding, C. V. CpG oligodeoxy-nucleotides act as adjuvants that switch on T helper 1 (Th1) immunity. The Journal of experimental medicine 186, 1623-1631 (1997).
non-patent document 5: Klinman, D. M. Immunotherapeutic uses of CpG oligodeoxynucleotides. Nature reviews. Immunology 4, 249-258 (2004).
non-patent document 6: Vollmer, J. & Krieg, A. M. Immunotherapeutic applications of CpG oligodeoxynucleotide TLR9 agonists. Advanced drug delivery reviews 61, 195-204 (2009).
non-patent document 7: Krug, A., et al. Identification of CpG oligonucleotide sequences with high induction of IFN-alpha/beta in plasmacytoid dendritic cells. European journal of immunology 31, 2154-2163 (2001).
non-patent document 8: Verthelyi, D., Ishii, K. J., Gursel, M., Takeshita, F. & Klinman, D. M. Human peripheral blood cells differentially recognize and respond to two distinct CPG motifs. Journal of immunology 166, 2372-2377 (2001).
non-patent document 9: Hartmann, G. & Krieg, A. M. Mechanism and function of a newly identified CpG DNA motif in human primary B cells. Journal of immunology 164, 944-953 (2000).
non-patent document 10: Hartmann, G., et al. Rational design of new CpG oligonucleotides that combine B cell activation with high IFN-alpha induction in plasmacytoid dendritic cells. European journal of immunology 33, 1633-1641 (2003).
non-patent document 11: Marshall, J. D., et al. Identification of a novel CpG DNA class and motif that optimally stimulate B cell and plasmacytoid dendritic cell functions. Journal of leukocyte biology 73, 781-792 (2003).
non-patent document 12: Samulowitz, U., et al. A novel class of immune-stimulatory CpG oligodeoxynucleotides unifies high potency in type I interferon induction with preferred structural properties. Oligonucleotides 20, 93-101 (2010).
non-patent document 13: Kerkmann, M., et al. Spontaneous formation of nucleic acid-based nanoparticles is responsible for high interferon-alpha induction by CpG-A in plasmacytoid dendritic cells. The Journal of biological chemistry 280, 8086-8093 (2005).
non-patent document 14: Klein, D. C., Latz, E., Espevik, T. & Stokke, B. T. Higher order structure of short immuno-stimulatory oligonucleotides studied by atomic force microscopy. Ultra microscopy 110, 689-693 (2010).
non-patent document 15: Puig, M., et al. Use of thermolytic protective groups to prevent G-tetrad formation in CpG ODN D type: structural studies and immunomodulatory activity in primates. Nucleic acids research 34, 6488-6495 (2006).
non-patent document 16: Bode, C., Zhao, G., Steinhagen, F., Kinjo, T. & Klinman, D. M. CpG DNA as a vaccine adjuvant. Expert review of vaccines 10, 499-511 (2011).
non-patent document 17: McHutchison, J. G., et al. Phase 1B, randomized, double-blind, dose-escalation trial of CPG 10101 in patients with chronic hepatitis C virus. Hepatology 46, 1341-1349 (2007).
non-patent document 18: Okamura, K., et al. Clinical evaluation of schizophyllan combined with irradiation in patients with cervical cancer. A randomized controlled study. Cancer 58, 865-872 (1986).
non-patent document 19: Oba, K.; Kobayashi, M.; Matsui, T.; Kodera, Y.; Sakamoto, J. Individual patient based meta-analysis of lentinan for unresectable/recurrent gastric cancer. Anticancer Res., 2009, 29, 2739-2746.
non-patent document 20: Nakano, H.; Namatame, K.; Nemoto, H.; Motohashi, H.; Nishiyama, K.; Kumada, K. A multi-institutional prospective study of lentinan in advanced gastric cancer patients with unresectable and recurrent diseases: Effect on prolongation of survival and improvement of quality of life. Hepato-Gastroenterol., 1999, 46, 2662-2668.
non-patent document 21: Sakurai, K., Mizu, M. & Shinkai, S. Polysaccharide-polynucleotide complexes. 2. Complementary polynucleotide mimic behavior of the natural polysaccharide schizophyllan in the macromolecular complex with single-stranded RNA and DNA. Biomacromolecules 2, 641-650 (2001).
non-patent document 22: Shimada, N., et al. A polysaccharide carrier to effectively deliver native phosphodiester CpG DNA to antigen-presenting cells. Bioconjugate chemistry 18, 1280-1286 (2007).
non-patent document 23: Koyama, S., et al. Plasmacytoid dendritic cells delineate immunogenicity of influenza vaccine subtypes. Science translational medicine 2, 25ra24 (2010).
non-patent document 24: Minari, J., et al. Enhanced cytokine secretion from primary macrophages due to Dectin-1 mediated uptake of CpG DNA/beta-1,3-glucan complex. Bioconjugate chemistry 22, 9-15 (2011).

SUMMARY OF THE INVENTION

Problems to be Solved by the Invention

The problem to be solved by the present invention is to provide an immunostimulating agent having a stronger activity than conventional CpG-SPG complexes.

Means of Solving the Problems

The present inventors have conducted intensive studies and identified a novel complex comprising K type CpG ODN (K3) (SEQ ID NO: 2) having a poly(dA) tail at the 3'-end and SPG, namely K3-SPG. It forms a high-order nano-particle that can be completely solubilized. Similarly, the present inventors have also succeeded in producing a novel complex K3-LNT comprising the aforementioned K type CpG ODN and lentinan (LNT). Although K3-SPG and K3-LNT do not have a D type CpG ODN sequence, it simultaneously has an immunostimulating activity unique to K type CpG ODN (e.g., activity to activate B cells (preferably, human B cells) to produce IL-6), and an immunostimulating activity unique to D type CpG ODN (e.g., activity to activate plasma cell-like dendritic cells to produce IFN-α). Furthermore, K3-LNT and K3-SPG have a potent vaccine adjuvant activity and, when inoculated together with an antigen for immunization, they induce both antigen specific humoral immunity and cellular immunity, and indeed showed a very potent infection-protective effect against RSV virus and influenza virus. They have further studied based on these findings and completed the present invention.

Accordingly, the present invention provides the following.

[1] An oligodeoxynucleotide comprising humanized K type CpG oligodeoxynucleotide and poly deoxyadenylate, wherein the poly deoxyadenylate is placed on the 3'-side of the humanized K type CpG oligodeoxynucleotide.

[2] The oligodeoxynucleotide of [1], wherein the humanized K type CpG oligodeoxynucleotide has a length of not less than 10 nucleotides, and comprises a nucleotide sequence represented by the formula:

5'$N_1N_2N_3$T-CpG-W$N_4N_5N_6$3' wherein CpG motif in the center is not methylated, W is A or T, and $N_1$, $N_2$, $N_3$, $N_4$, $N_5$ and $N_6$ may be any nucleotides.

[3] The oligodeoxynucleotide of [1] or [2], wherein the humanized K type CpG oligodeoxynucleotide consists of the nucleotide sequence shown by SEQ ID NO: 1.

[4] The oligodeoxynucleotide of any of [1]-[3], wherein phosphodiester bonds in the oligodeoxynucleotide are partly or entirely substituted by phosphorothioate bonds.

[5] The oligodeoxynucleotide of [4], wherein the phosphodiester bonds in the oligodeoxynucleotide are entirely substituted by phosphorothioate bonds.

[6] The oligodeoxynucleotide of any of [1]-[5], wherein the poly deoxyadenylate has a length of 20-60 nucleotides.

[7] A complex comprising the oligodeoxynucleotide of any of [1]-[6] and β-1,3-glucan.

[8] The complex of [7], wherein the β-1,3-glucan is lentinan, schizophyllan, scleroglucan, curdlan, pachyman, grifolan, or laminaran.

[9] The complex of [8], wherein the β-1,3-glucan is lentinan, schizophyllan or scleroglucan.

[10] A complex consisting of an oligodeoxynucleotide described in the following (i), and β-1,3-glucan described in (ii):
(i) an oligodeoxynucleotide wherein poly deoxyadenylate of 20-60 nucleotide length is bound at the 3'-end of an oligodeoxynucleotide consisting of the nucleotide sequence shown by SEQ ID NO: 1, and all of the phosphodiester bonds are substituted by phosphorothioate bonds
(ii) lentinan or schizophyllan.

[11] The complex of any of [7]-[10], having a triple helix structure.

[12] The complex of any of [7]-[11], having an activity to activate B cells to produce IL-6, and an activity to activate dendritic cells to produce IFN-α.

[13] A pharmaceutical composition comprising the oligodeoxynucleotide of any of [1]-[6], or the complex of any of [7]-[12].

[14] The pharmaceutical composition of [13], which is for the prophylaxis or treatment of virus infection, cancer, an allergic disease, or intracellular parasitic protozoan or bacterial infection.

[15] The pharmaceutical composition of [14], which is for the prophylaxis or treatment of virus infection.

[16] The pharmaceutical composition of [15], wherein the virus infection is RS virus or influenza virus infection.

[17] An agent for inducing production of type I and/or type II interferon, comprising the complex of any of [7]-[12].

[18] An immunostimulating agent comprising the oligodeoxynucleotide of any of [1]-[6], or the complex of any of [7]-[12].

[19] The immunostimulating agent of [18], which is a vaccine adjuvant.

[20] A prophylactic or therapeutic agent for virus infection, cancer, an allergic disease, or intracellular parasitic protozoan or bacterial infection, comprising the oligodeoxynucleotide of any of [1]-[6], or the complex of any of [7]-[12].

[21] The prophylactic or therapeutic agent of [20], wherein the virus infection is RS virus or influenza virus infection.

[22] Use of the oligodeoxynucleotide of any of [1]-[6], or the complex of any of [7]-[12], for the production of a pharmaceutical composition.

[23] The use of [22], wherein the pharmaceutical composition is a pharmaceutical composition for the prophylaxis or treatment of virus infection, cancer, an allergic disease, or intracellular parasitic protozoan or bacterial infection.

[24] The use of [23], wherein the virus infection is RS virus or influenza virus infection.

[25] A method for the treatment or prophylaxis of a disease in a warm-blooded animal, comprising administering a pharmacologically effective amount of the oligodeoxynucleotide of any of [1]-[6], or the complex of any of [7]-[12] to the warm-blooded animal.

[26] The method of [25], wherein the disease is virus infection, cancer, an allergic disease, or intracellular parasitic protozoan or bacterial infection.

[27] The method of [26], wherein the virus infection is RS virus or influenza virus infection.

[28] The method of any of [25]-[27], wherein the warm-blooded animal is human.

[29] A method of inducing a protective immune reaction in a warm-blooded animal, comprising administering a pharmacologically effective amount of the oligodeoxynucleotide of any of [1]-[6], or the complex of any of [7]-[12] to the warm-blooded animal.

[30] The oligodeoxynucleotide of any of [1]-[6], or the complex of any of [7]-[12], for use for the treatment or prophylaxis of virus infection, cancer, an allergic disease, or intracellular parasitic protozoan or bacterial infection.

[31] The oligodeoxynucleotide or complex of [30], wherein the virus infection is RS virus or influenza virus infection.

[32] A pharmaceutical composition comprising
(a) the oligodeoxynucleotide of any of [1]-[6], or the complex of any of [7]-[12], and
(b) an antigen.

[33] The composition of [32], which is for inducing an immune reaction to the antigen.

[34] The composition of [33], wherein the antigen is derived from a pathogen.

[35] The composition of [34], which is for the prophylaxis or treatment of infection with the pathogen.

[36] The composition of [35], wherein the pathogen is a virus.

[37] The composition of [36], wherein the virus is an RS virus or influenza virus.

Effect of the Invention

The present invention provides an oligodeoxynucleotide having a superior immunostimulating activity and a complex containing same. Particularly, the complex of the present invention concurrently has an immunostimulating activity unique to K type CpG ODN, and an immunostimulating activity unique to D type CpG ODN. Furthermore, since the complex of the present invention has a strong vaccine adjuvant activity, when immunization with the complex of the present invention together with an antigen is performed, both the antigen specific humoral immunity and cellular immunity are stimulated to provide a highly strong infection protective effect. Therefore, the complex of the present invention is useful as an immunostimulating agent or vaccine adjuvant.

DESCRIPTION OF EMBODIMENTS

1. Oligodeoxynucleotide

Figure 1:
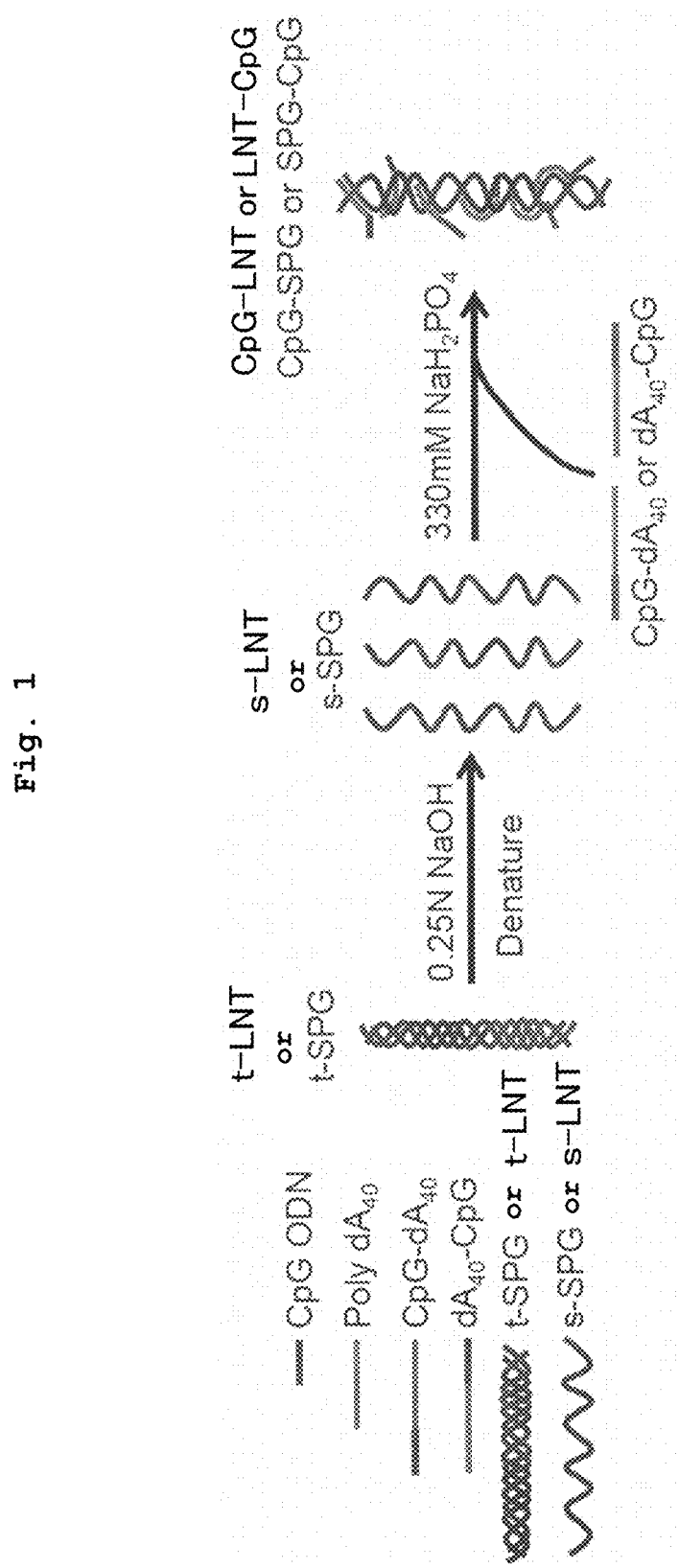
FIG. 1 shows a complexation method of CpG ODN and LNT or SPG.

The present invention provides an oligodeoxynucleotide comprising K type CpG oligodeoxynucleotide and poly deoxyadenylate (dA) (hereinafter to be referred to as the oligodeoxynucleotide of the present invention).

The oligodeoxynucleotide of the present invention includes one wherein the phosphodiester bonds are modified (e.g., a part of or all phosphodiester bonds is/are substituted by a phosphorothioate bond).

The oligodeoxynucleotide of the present invention includes pharmaceutically acceptable salts.

In the present specification, oligodeoxynucleotide and ODN mean the same. In addition, the "humanized K type CpG oligodeoxynucleotide (CpG ODN)" and "humanized K type CpG oligodeoxynucleotide (CpG ODN) residue" mean the same regardless of the presence or absence of the term "residue" at the end, and are used exchangeably. Furthermore, poly deoxyadenylate and poly deoxyadenosine acid (residue) mean the same. The term "residue" means a partial structure of a compound having a higher molecular weight. Those of ordinary skill in the art can easily understand from the context whether the "humanized K type CpG oligodeoxynucleotide (CpG ODN)" means an independent molecule, or a partial structure of a compound having a higher molecular weight in the present specification. The same applies to the terms relating to other partial structures contained in the oligodeoxynucleotide of the present invention, such as "poly deoxyadenylate" and the like.

CpG oligodeoxynucleotide (CpG ODN) is a single strand DNA containing an immunostimulatory non-methylated CpG motif, and is a TLR9 agonist. CpG ODN includes 4 types of K type (also called B type), D type (also called A type), C type and P type, which are different in the backbone, sequence and immunostimulating property (Advanced drug delivery reviews 61, 195-204 (2009)). Of these, the oligodeoxynucleotide of the present invention comprises K type CpG ODN.

K type CpG ODN is a CpG ODN having structural and functional properties that it typically contains non-palindromic, plural non-methylated CpG motifs, activates B cells to produce IL-6, but scarcely induces IFN-α production by plasma cell-like dendritic cells (pDCs). Non-methylated CpG motif is a short nucleotide sequence containing at least one cytosine (C)-guanine (G) sequence, wherein the 5-position of cytosine in the cytosine-guanine sequence is not methylated. In the following explanation, CpG means non-methylated CpG, unless particularly indicated. Therefore, the oligodeoxynucleotide of the present invention has an immunostimulating activity unique to K type CpG ODN (e.g., activity to activate B cells (preferably, human B cells) to produce IL-6) by containing K type CpG ODN. Many humanized K type CpG ODNs are known in the pertinent technical field (Journal of immunology 166, 2372-2377 (2001); Journal of immunology 164, 944-953 (2000); U.S. Pat. No. 8,030,285 B2).

The K type CpG ODN comprised in the oligodeoxynucleotide of the present invention is preferably humanized. Being "humanized" means that it has an agonist activity on human TLR9. Therefore, the oligodeoxynucleotide of the present invention comprising humanized K type CpG ODN has an immunostimulating activity for human, which is unique to K type CpG ODN (e.g., activity to activate human B cells to produce IL-6).

K type CpG ODN preferably used in the present invention has a length of not less than 10 nucleotides and contains a nucleotide sequence represented by the formula:

5'$N_1N_2N_3$T-CpG-W$N_4N_5N_6$3' wherein CpG motif in the center is not methylated, W is A or T, and $N_1$, $N_2$, $N_3$, $N_4$, $N_5$ and $N_6$ may be any nucleotide.

In one embodiment, the K type CpG ODN in the present invention has a length of not less than 10 nucleotides and contains a nucleotide sequence represented by the above-mentioned formula. In the above-mentioned formula, the CpG motif of 4 bases (TCpGW) in the center only needs to be contained in the 10 nucleotides, and does not need to be located between $N_3$ and $N_4$ in the above-mentioned formula. In addition, $N_1$, $N_2$, $N_3$, $N_4$, $N_5$ and $N_6$ in the above-mentioned formula may be any nucleotides, and the combination of at least one (preferably one) of $N_1$ and $N_2$, $N_2$ and $N_3$, $N_3$ and $N_4$, $N_4$ and $N_5$, and $N_5$ and $N_6$ may form a 2 base CpG motif. When the aforementioned CpG motif with 4 bases is not located between $N_3$ and $N_4$, any 2 continuous bases in the 4 bases in the center (4th-7th bases) of the above-mentioned formula is the CpG motif, and other 2 bases may be any nucleotides.

K type CpG ODN more preferably used in the present invention contains a non-palindromic structure containing one or plural CpG motifs. K type CpG ODN further preferably used in the present invention consists of a non-palindromic structure containing one or plural CpG motifs.

Humanized K type CpG ODN is generally characterized by CpG motif consisting of 4 bases of TOGA or TCGT. In many cases, 2 or 3 of such 4 base CpG motif are contained in one humanized K type CpG ODN. Therefore, in a preferable embodiment, K type CpG ODN contained in the oligodeoxynucleotide of the present invention contains at least one, more preferably two or more, further preferably 2 or 3, of 4 base CpG motifs consisting of TOGA or TCGT. When the K type CpG ODN has 2 or 3 of 4 base CpG motifs, these 4 base CpG motifs may be the same or different, and is not particularly limited as long as it has an agonist activity on human TLR9.

K type CpG ODN contained in the oligodeoxynucleotide of the present invention more preferably comprises the nucleotide sequence shown by SEQ ID NO: 1.

While the length of the K type CpG ODN is not particularly limited as long as the oligodeoxynucleotide of the present invention has an immunostimulating activity (e.g., activity that activates B cells (preferably, human B cells) to produce IL-6), it is preferably not more than 100 nucleotide length (e.g., 10-75 nucleotide length). The length of the K type CpG ODN is more preferably not more than 50 nucleotide length (e.g., 10-40 nucleotide length). The length of the K type CpG ODN is more preferably not more than 30 nucleotide length (e.g., 10-25 nucleotide length). The length of the K type CpG ODN is most preferably 12-25 nucleotide length.

While the length of the poly deoxyadenylate (dA) is not particularly limited as long as it is sufficient to form a triple helix structure with β-1,3-glucan (preferably, lentinan, or schizophyllan) chain, from the aspects of forming a stable triple helix structure, it is generally not less than 20 nucleotide length, preferably not less than 40 nucleotide length, further preferably not less than 60 nucleotide length. Theoretically, poly dA does not have the upper limit of the length, since a longer poly dA forms a stabler triple helix structure with β-1,3-glucan. However, when it is too long, the length of oligodeoxynucleotide varies at synthesis. Therefore, it is generally not more than 100, preferably not more than 80, nucleotide length. On the other hand, from the aspects of formation of the aforementioned stable triple helix structure, as well as increase in the amount of the oligodeoxynucleotide of the present invention that binds per unit amount of β-1,3-glucan, avoidance of the length variability at synthesis of the oligodeoxynucleotide, and complexation efficiency, the length of the poly dA is preferably 20-60 nucleotide length (specifically, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotide length), more preferably 30-50 nucleotide length (30, 31, 32, 33, 34, 35, 36, 37, 38, 39, 40, 41, 42, 43, 44, 45, 46, 47, 48, 49, 50 nucleotide length), most preferably 30-45 nucleotide length (30, 31, 32, 33, 34, 35, 36, 37, 38, 39, 40, 41, 42, 43, 44, 45 nucleotide length). Particularly, when it is not less than 30 nucleotide length, good complexation efficiency is achieved. The oligodeoxynucleotide of the present invention containing poly dA has an activity to form a triple helix structure with two schizophyllan chains. Note that poly deoxyadenylate is sometimes indicated as "poly (dA)" or "poly(dA)".

While one molecule of the oligodeoxynucleotide of the present invention may contain plural K type CpG ODNs and/or poly dAs, it preferably contains one each of K type CpG ODN and poly dA, most preferably consists of one each of K type CpG ODN and poly dA.

The oligodeoxynucleotide of the present invention is characterized in that poly dA is placed at the 3'-side of K type CpG ODN. By this arrangement, the complex of the present invention (detail to be described below) comes to have an immunostimulating activity unique to K type CpG ODN as well as an immunostimulating activity unique to D type CpG ODN.

K type CpG ODN and poly dA may be directly linked by a covalent bond, or linked via a spacer sequence. The spacer sequence means a nucleotide sequence having one or more nucleotides to be inserted between two adjacent constituent elements. While the length of the spacer sequence is not particularly limited as long as the complex of the present invention has an immunostimulating activity (preferably activity to activate B cells to produce IL-6, and activity to activate dendritic cells to produce IFN-α), it is generally 1-nucleotide length, preferably 1-5 nucleotide length, more preferably 1-3 nucleotide length. Most preferably, K type CpG ODN and poly dA are directly linked by a covalent bond.

The oligodeoxynucleotide of the present invention optionally has an additional nucleotide sequence at the 5'-end and/or the 3'-end thereof, in addition to K type CpG ODN, poly dA and an optional spacer sequence. While the length of the additional nucleotide sequence is not particularly limited as long as the complex of the present invention has an immunostimulating activity (preferably activity to activate B cells to produce IL-6, and activity to activate dendritic cells to produce IFN-α), it is generally 1-10 nucleotide length, preferably 1-5 nucleotide length, more preferably 1-3 nucleotide length.

In a preferable embodiment, the oligodeoxynucleotide of the present invention does not contain such additional nucleotide sequence at the 5'-end and/or the 3'-end. That is, the oligodeoxynucleotide of the present invention preferably consists of K type CpG ODN, poly dA and an optional spacer sequence, more preferably consists of K type CpG ODN and poly dA.

In a most preferable embodiment, the oligodeoxynucleotide of the present invention consists of K type CpG ODN (specifically, for example, oligodeoxynucleotide consisting of the nucleotide sequence shown by SEQ ID NO: 1) and poly dA, wherein K type CpG ODN is present at the 5'-end of the oligodeoxynucleotide and poly dA is present at the 3'-end thereof. Specifically, it is an oligodeoxynucleotide wherein poly dA of 20-60 nucleotide length (more preferably, 30-50 nucleotide length (30, 31, 32, 33, 34, 35, 36, 37, 38, 39, 40, 41, 42, 43, 44, 45, 46, 47, 48, 49, 50 nucleotide length), most preferably, 30-45 nucleotide length (30, 31, 32, 33, 34, 35, 36, 37, 38, 39, 40, 41, 42, 43, 44, 45 nucleotide length)) is bound at the 3'-end of an oligodeoxynucleotide consisting of the nucleotide sequence shown by SEQ ID NO: 1, for example, an oligodeoxynucleotide consisting of the nucleotide sequence shown by SEQ ID NO: 2, or 9-12.

The full-length of the oligodeoxynucleotide of the present invention is generally 30-200 nucleotide length, preferably 35-100 nucleotide length, more preferably 40-80 nucleotide length (specifically, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 nucleotide length), further preferably 50-70 nucleotide length (specifically, 50, 51, 52, 53, 54, 55, 56, 57, 58, 59, 60, 61, 62, 63, 64, 65, 66, 67, 68, 69, 70 nucleotide length), most preferably 50-65 nucleotide length (specifically, 50, 51, 52, 53, 54, 55, 56, 57, 58, 59, 60, 61, 62, 63, 64, 65 nucleotide length).

The oligodeoxynucleotide of the present invention may be appropriately modified to be resistant to degradation in vivo (e.g., degradation by exo- or endonuclease). Preferably, the modification includes phosphorothioate modification and phosphorodithioate modification. That is, a part of or all phosphodiester bonds in the oligodeoxynucleotide of the present invention is/are substituted by a phosphorothioate bond or phosphorodithioate bond.

Preferably, the oligodeoxynucleotide of the present invention includes modification of a phosphodiester bond, more preferably, the modification of the phosphodiester bond is a phosphorothioate bond (that is, as described in WO 95/26204, one of the non-crosslinking oxygen atoms is substituted by a sulfur atom). That is, a part of or all phosphodiester bonds in the oligodeoxynucleotide of the present invention is/are substituted by a phosphorothioate bond.

The oligodeoxynucleotide of the present invention preferably contains modification by a phosphorothioate bond or a phosphorodithioate bond in K type CpG ODN, more preferably, all phosphodiester bonds in the K type CpG ODN are substituted by phosphorothioate bonds. Also, the oligodeoxynucleotide of the present invention preferably contains a phosphorothioate bond or a phosphorodithioate bond in poly dA, more preferably, all phosphodiester bonds in the poly dA are substituted by phosphorothioate bonds. Further preferably, all phosphodiester bonds in the oligodeoxynucleotide of the present invention comprising the humanized K type CpG oligodeoxynucleotide and poly deoxyadenylate are substituted by phosphorothioate bonds. Most preferably, the oligodeoxynucleotide of the present invention is an oligodeoxynucleotide wherein poly dA of 20-60 nucleotide length (more preferably, 30-50 nucleotide length (30, 31, 32, 33, 34, 35, 36, 37, 38, 39, 40, 41, 42, 43, 44, 45, 46, 47, 48, 49, 50 nucleotide length), most preferably, 30-45 nucleotide length (30, 31, 32, 33, 34, 35, 36, 37, 38, 39, 40, 41, 42, 43, 44, 45 nucleotide length)) is bound to the 3'-end of humanized K type CpG oligodeoxynucleotide (e.g., SEQ ID NO: 1), and all phosphodiester bonds contained in the oligodeoxynucleotide are substituted by phosphorothioate bonds. Due to the phosphorothioate bond, the oligodeoxynucleotide of the present invention is expected to show not only the resistance to degradation but also enhancement of an immunostimulating activity (e.g., activity to activate B cells to produce IL-6), and a high yield of CpG-β-1,3-glucan complex. In the present specification, the phosphorothioate bond means the same as a phosphorothioate backbone, and the phosphodiester bond means the same as a phosphate backbone.

The oligodeoxynucleotide of the present invention includes any pharmaceutically acceptable salts, ester, and salts of such ester, of the above-mentioned oligodeoxynucleotide.

Preferable examples of the pharmaceutically acceptable salts of the oligodeoxynucleotide of the present invention include metal salts such as alkali metal salts (e.g., sodium salt, potassium salt, and lithium salt), alkaline earth metal salts (e.g., calcium salt, and magnesium salt), aluminum salt, iron salt, zinc salt, copper salt, nickel salt, cobalt salt and the like; amine salts such as inorganic salts (e.g., ammonium salt), and organic salts (e.g., t-octylamine salt, dibenzylamine salt, morpholine salt, glucosamine salt, phenylglycine alkylester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzyl-phenethylamine salt, piperazine salt, tetramethylammonium salt, tris(hydroxymethyl)aminomethane salt) and the like; inorganic acid salts such as halogenated hydracid salts (e.g., hydrofluoride, hydrochloride, hydrobromide, hydroiodide), nitrate salt, perchlorate, sulfate, phosphate and the like;

organic acid salts such as lower alkanesulfonates (e.g., methanesulfonate, trifluoromethanesulfonate, ethanesulfonate), arylsulfonates (e.g., benzenesulfonate, p-toluenesulfonate), acetate, malate, fumarate, succinate, citrate, tartrate, oxalate, maleate and the like; and amino acid salts such as glycine salt, lysine salt, arginine salt, ornithine salt, glutamate and aspartate.

While the oligodeoxynucleotide of the present invention may take any form of a single strand, a double strand, and a triple strand, it is preferably a single strand.

The oligodeoxynucleotide of the present invention is preferably isolated. Being "isolated" means that an operation to remove factors other than the object components has been performed, and the oligodeoxynucleotide is not in the state of natural presence. The purity of the "isolated oligodeoxynucleotide" (percentage of weight of the object oligodeoxynucleotide in the total weight of the evaluation target product) is generally not less than 70%, preferably not less than 80%, more preferably not less than 90%, further preferably not less than 99%.

Since the oligodeoxynucleotide of the present invention has a superior immunostimulating activity (e.g., activity to activate B cells (preferably, human B cells) to produce IL-6), it is useful as an immunostimulating agent and the like. Furthermore, since the oligodeoxynucleotide of the present invention has the property to form a triple helix structure with two β-1,3-glucans (preferably, lentinan, schizophyllan, or scleroglucan), it is useful for the preparation of the complex of the present invention mentioned below.

2. Complex

The present invention provides a complex containing the above-mentioned oligodeoxynucleotide of the present invention and β-1,3-glucan (hereinafter to be referred to as the complex of the present invention).

Since the aforementioned oligodeoxynucleotide of the present invention contains K type CpG ODN, it shows, by itself, an immunostimulating activity unique to K type CpG ODN (e.g., activity to activate B cells (preferably, human B cells) to produce IL-6), and is poor in an immunostimulating activity unique to D type CpG ODN (e.g., activity to activate plasma cell-like dendritic cells to produce IFN-α). Surprisingly, however, it acquires an immunostimulating activity unique to D type CpG ODN (e.g., activity to activate plasma cell-like dendritic cells to produce IFN-α) by forming a complex with β-1,3-glucan (preferably, lentinan, or schizophyllan), without requiring the sequence of D type CpG ODN. That is, the complex of the present invention has both an immunostimulating activity unique to K type CpG ODN (e.g., activity to activate B cells (preferably, human B cells) to produce IL-6), and an immunostimulating activity unique to D type CpG ODN (e.g., activity to activate plasma cell-like dendritic cells (preferably human plasma cell-like dendritic cells) to produce IFN-α.

Examples of β-1,3-glucan used in the present invention include lentinan, schizophyllan, scleroglucan, curdlan, pachyman, grifolan, laminaran and the like. The β-1,3-glucan is preferably one containing many 1,6-glucopyranoside branches (side chain rate 33-40%) such as lentinan, schizophyllan and scleroglucan, more preferably lentinan, or schizophyllan, most preferably lentinan.

Lentinan (LNT) is a known β-1,3-1,6-glucan derived from shiitake mushroom and having a molecule formula of $(C_6H_{10}O_5)n$, and a molecular weight of about 300,000-700,000. Although it is hardly soluble in water, methanol, ethanol(95) and acetone, it is soluble in polar organic solvents (DMSO) and an aqueous sodium hydroxide solution.

Lentinan has an action to enhance activated macrophage, killer T cells, natural killer cells and antibody-dependent macrophage-mediated cytotoxic (ADMC) activity (Hamuro, J., et al.: Immunology, 39, 551-559, 1980, Hamuro, J., et al.: Int. J. Immunopharmacol., 2, 171, 1980, Herlyn, D., et al.: Gann, 76, 37-42, 1985). In animal experiments, combined administration with a chemotherapeutic agent showed a tumor growth suppressive action and a life-prolonging effect on syngeneic tumor and autologous tumor. Also, an administration of lentinan alone showed a tumor growth suppressive action and a life-prolonging effect. In clinical tests, a combined use with tegafur oral administration prolonged the survival period of inoperable or recurrent gastric cancer patients (pharmaceutical product interview form "lentinan intravenous injection 1 mg" Ajinomoto Co., Inc.), and has been approved in Japan. The effect of administration of lentinan alone has not been confirmed to date.

Schizophyllan (SPG) is a known soluble β-glucan derived from *Schizophyllum commune*. SPG consists of the main chain of β-(1→3)-D-glucan, and one β-(1→6)-D-glucosyl side chain per 3 glucoses (Tabata, K., Ito, W., Kojima, T., Kawabata, S. and Misaki A., "Carbohydr. Res.", 1981, 89, 1, p. 121-135). SPG has been actually used for 20 years or more as an intramuscular injection preparation clinical drug for immunoadjuvant therapy of gynecologic cancer (Shimizu, Chin, Hasumi, Masubuchi, "Biotherapy", 1990, 4, p. 1390 Hasegawa, "Oncology and Chemotherapy", 1992, 8, p. 225), and in vivo safety has been confirmed (Theresa, M. McIntire and David, A. Brant, "J. Am. Chem. Soc.", 1998, 120, p. 6909).

In the present specification, "complex" means a product obtained by association of plural molecules via a noncovalent bond or a covalent bond such as electrostatic bond, van der Waals bond, hydrogen bond, hydrophobicity interaction and the like.

The complex of the present invention preferably exhibits a triple helix structure. In a preferable embodiment, of the three chains forming the triple helix structure, two are β-1,3-glucan chains, and one is a chain of poly deoxyadenylate in the above-mentioned oligodeoxynucleotide of the present invention. The complex may contain a part not forming the triple helix structure.

The composition ratio of oligodeoxynucleotide and β-1,3-glucan in the complex of the present invention may vary depending on the chain length of poly deoxyadenylate in the oligodeoxynucleotide, the length of β-1,3-glucan and the like. For example, when length of the β-1,3-glucan chain and poly deoxyadenylate chain is equivalent, two β-1,3-glucan chains and one oligodeoxynucleotide of the present invention may be associated to form a triple helix structure. In general, since the chain length of poly deoxyadenylate is shorter than that of β-1,3-glucan chain, plural oligodeoxynucleotides of the present invention may be associated with two β-1,3-glucan chain via poly deoxyadenylate to form a triple helix structure (see FIG. 1).

The complex of the present invention is a complex containing humanized K type CpG ODN and β-1,3-glucan (e.g., lentinan, schizophyllan, scleroglucan, curdlan, pachyman, grifolan, laminaran), preferably a complex consisting of humanized K type CpG ODN and β-1,3-glucan (e.g., lentinan, schizophyllan, scleroglucan). More preferably, it is a complex consisting of an oligodeoxynucleotide wherein a poly deoxyadenylate of 20-60 nucleotide length (specifically, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotide length) is bound to the 3'-side of an oligodeoxynucleotide consisting of the nucleotide sequence shown by SEQ ID NO: 1, and all phosphodiester bonds are substituted by phosphorothioate bonds, and β-1,3-glucan (e.g., lentinan, schizophyllan) (e.g., K3-dA20-60-LNT, K3-dA20-60-SPG), further preferably, it is a complex consisting of an oligodeoxynucleotide wherein a poly deoxyadenylate of 30-50 nucleotide length (specifically, 30, 31, 32, 33, 34, 35, 36, 37, 38, 39, 40, 41, 42, 43, 44, 45, 46, 47, 48, 49, 50 nucleotide length) is bound to the 3'-side of an oligodeoxynucleotide consisting of the nucleotide sequence shown by SEQ ID NO: 1, and all phosphodiester bonds are substituted by phosphorothioate bonds, and β-1,3-glucan (e.g., lentinan, schizophyllan) (e.g., K3-dA30-50-LNT, K3-dA30-50-SPG), most preferably, it is a complex consisting an oligodeoxynucleotide wherein a poly deoxyadenylate of 30-45 nucleotide length (specifically, 30, 31, 32, 33, 34, 35, 36, 37, 38, 39, 40, 41, 42, 43, 44, 45 nucleotide length) is bound to the 3'-side of an oligodeoxynucleotide consisting of the nucleotide sequence shown by SEQ ID NO: 1, and all phosphodiester bonds are substituted by phosphorothioate bonds, and β-1,3-glucan (e.g., lentinan, schizophyllan) (K3-dA30-45-LNT, K3-dA30-45-SPG).

The preparation method of the complex of the present invention can be performed under the conditions similar to those described in non-patent documents 21-24, and JP-A-2008-100919. That is, β-1,3-glucan which is inherently naturally present as a triple helix structure is dissolved in an aprotic organic polar solvent (dimethyl sulfoxide (DMSO), acetonitrile, acetone etc.) or an aqueous alkaline solution (sodium hydroxide, potassium hydroxide, ammonia, calcium hydroxide etc.) to be loosened into a single strand. A solution of the thus-obtained single strand β-1,3-glucan and a solution (aqueous solution, buffered aqueous solution at near neutral pH, or acidic buffered aqueous solution, preferably, aqueous solution or buffered aqueous solution at near neutral pH) of the oligodeoxynucleotide of the present invention are mixed, the pH is adjusted to a near neutral pH as necessary, and the mixture is maintained for a suitable time, for example, overnight at 5° C. As a result, two β-1,3-glucan chains and a poly dA chain in the oligodeoxynucleotide form a triple helix structure, whereby the complex of the present invention can be formed. The resulting complex can be subjected to purification by size-exclusion chromatography, ultrafiltration, dialysis and the like to remove oligodeoxynucleotide not forming the complex. In addition, the resulting complex can be subjected to purification by anion exchange chromatography to remove β-1,3-glucan not forming the complex. The complex can be appropriately purified by the above-mentioned methods.

Formation of the complex of the present invention can be confirmed by, for example, measuring conformation change by CD (circular dichroism) spectrum, UV absorption shift by size-exclusion chromatography, gel electrophoresis, microchip electrophoresis, capillary electrophoresis, though the method is not limited thereto.

While of the mixing ratio of the oligodeoxynucleotide of the present invention and β-1,3-glucan can be appropriately determined in consideration of the length of poly dA chain and the like, the molar ratio (SPG/ODN) is generally 0.02-2.0, preferably 0.1-0.5. In a further embodiment, the molar ratio (β-1,3-glucan (LNT etc.)/ODN) is, for example, 0.005-1.0, preferably 0.020-0.25.

The preparation method of the complex of the present invention is explained by taking CpG-ODN and LNT complex as an example. LNT is dissolved in 0.05-2N, preferably 0.1-1.5N, alkaline aqueous solution (e.g., 0.25N aqueous sodium hydroxide solution), and the mixture is left standing at 1° C.-40° C. for hr-4 days (e.g., stood overnight at room temperature) to prepare an aqueous single strand LNT solution (e.g., 50 mg/ml aqueous LNT solution). The aforementioned aqueous LNT solution and aqueous CpG solution (e.g., 100 μM aqueous CpG solution) prepared separately are mixed at a molar ratio (LNT/ODN) of 0.005-1.0, then the aforementioned LNT aqueous solution is neutralized with buffered acidic aqueous solution (e.g., $NaH_2PO_4$) and maintained at 1-40° C. for 6 hr-4 days (e.g., overnight at 4° C.) to complete complexation. LNT aqueous solution may be added lastly and mixed for the aforementioned complexation. Formation of the complex can be confirmed by, for example, shift of CpG ODN to the high molecular weight side by size-exclusion chromatography, while monitoring the absorption at 240-280 nm (e.g., 260 nm).

In one embodiment, the complex of the present invention exhibits the form of rod-shaped particles. The particle size is equivalent to that of a particle naturally formed by β-1,3-glucan (e.g., schizophyllan), used as the material, by exhibiting a triple helix structure. An average particle size is generally 10-100 nm, preferably 20-50 nm. The particle size can be measured by dissolving a complex in water, and subjecting the solution to a dynamic light scattering method at 80° C. by using Malvern Instruments Zeta Sizer.

The complex of the present invention is preferably isolated. The purity of the "isolated complex" (percentage of weight of object complex to total weight of evaluation target products) is generally not less than 70%, preferably not less than 80%, more preferably not less than 90%, further preferably not less than 99%.

Since the complex of the present invention has a superior immunostimulating activity and has both an immunostimulating activity unique to K type CpG ODN (e.g., activity to activate B cells (preferably, human B cells) to produce IL-6), and an immunostimulating activity unique to D type CpG ODN (e.g., activity to activate plasma cell-like dendritic cells (preferably human plasma cell-like dendritic cells) to produce IFN-α, it is useful as an immunostimulating agent and the like. For example, a complex containing K type CpG ODN (e.g., SEQ ID NO: 2, 11, 12) and LNT (K3-LNT) and a complex containing K type CpG ODN (e.g., SEQ ID NO: 2) and SPG (K3-SPG) have an ability to induce inflammation response (pan-IFN-α, IL-6 etc.), an action to enhance an antigen-specific IgG antibody titer (Total IgG, IgG2c etc.) in the serum of a virus-inoculated individual, an ability to antigen-specifically produce cytokine (IFN-γ, IL2 etc.) in a virus-inoculated individual, and an infection protective effect against viruses. K3-LNT also has an ability to enhance production of Th2 cytokine (IL-13 etc.) in a virus-inoculated individual. Therefore, they are useful as novel vaccine adjuvant candidates.

3. Pharmaceutical Composition

The present invention provides a pharmaceutical composition comprising the above-mentioned oligodeoxynucleotide of the present invention or the above-mentioned complex of the present invention. The pharmaceutical composition of the present invention can be obtained by formulating the above-mentioned oligodeoxynucleotide of the present invention or the above-mentioned complex of the present invention according to a conventional means. The pharmaceutical composition of the present invention contains the oligodeoxynucleotide or complex of the present invention and a pharmacologically acceptable carrier. Also, the pharmaceutical composition may further contain an antigen. Such pharmaceutical composition is provided in a dosage form suitable for oral or parenteral administration.

As a composition for parenteral administration, for example, injection, suppository and the like are used, and injection may encompass dosage forms such as intravenous injection, subcutaneous injection, intradermal injection, muscular injection, drip injection and the like. Such injection can be prepared according to a known method. The preparation method of injection includes dissolving or suspending the above-mentioned oligodeoxynucleotide or complex of the present invention in an aseptic aqueous solvent generally used for injection. As the aqueous solvent for injection, for example, distilled water; physiological saline; buffers such as phosphate buffer, carbonate buffer, tris buffer, acetate buffer and the like; and the like can be used. The pH of such aqueous solvent is, for example, 5-10, preferably 6-8. Prepared injection is preferably filled in a suitable ampoule.

It is also possible to prepare a powder preparation of the oligodeoxynucleotide or complex of the present invention by subjecting a suspension of the oligodeoxynucleotide or complex of the present invention to a treatment such as vacuum drying, freeze-drying and the like. The oligodeoxynucleotide or complex of the present invention can be used by preserving same in a powder state, and dispersing the powder in an aqueous solvent for injection when in use.

The content of the oligodeoxynucleotide or complex of the present invention in a pharmaceutical composition is generally about 0.1-100 wt %, preferably about 1-99 wt %, more preferably about 10-90 wt %, of the whole pharmaceutical composition.

The pharmaceutical composition of the present invention may contain, as an active ingredient, the oligodeoxynucleotide or complex of the present invention alone or a combination of the oligodeoxynucleotide or complex of the present invention and other active ingredient.

4. Pharmaceutical Use

Since the oligodeoxynucleotide and complex of the present invention has a superior immunostimulating activity, the oligodeoxynucleotide, complex and pharmaceutical composition of the present invention can be used as immunostimulating agents. Administration of the oligodeoxynucleotide, complex or pharmaceutical composition of the present invention to a mammal (primates such as human and the like, rodents such as mouse and the like, etc.) can induce an immune reaction in the mammal. Particularly, since the complex of the present invention has a D type CpG ODN activation property, and stimulates peripheral blood mononuclear cells to produce large amounts of type I interferon (Pan-IFN-α, IFN-α2 etc.) and type II interferon (IFN-γ), it is useful as a type I interferon production inducing agent, type II interferon production inducing agent, or type I and type II interferon production inducing agent. Since the complex of the present invention and a pharmaceutical composition containing same induce production of both type I and type II interferons, they are useful for the prophylaxis or treatment of a disease for which either or both of type I and type II interferons is/are effective. Examples of the disease for which type I interferon is effective include virus infection (e.g., hepatitis C virus (HCV), herpes virus, papilloma virus, RS virus, influenza virus etc.), cancer and the like. Examples of the disease for which type II interferon is effective include allergic disease, infections with intracellular parasitic protozoan (*Leishmania* etc.), bacterium (*Listeria, Mycobacterium tuberculosis* etc.) and the like, and the like. As for acute virus infections with RS virus, influenza virus and the like, since both type I interferon and type II interferon enhance immune responses relating to the virus elimination, the complex and a pharmaceutical composition containing same of the present invention are expected to be effective for acute virus infections.

Also, the oligodeoxynucleotide and complex of the present invention, particularly, the complex of the present invention, have a strong vaccine adjuvant activity, and administration of the oligodeoxynucleotide and complex of the present invention together with an antigen to a mammal can induce a strong immune reaction to the antigen. Therefore, the present invention also provides a composition for inducing an immune reaction to an antigen, which contains (a) the oligodeoxynucleotide of the present invention, or the complex of the present invention, and (b) the antigen. Particularly, the complex of the present invention strongly induces both a humoral immune reaction to an antigen (antigen-specific antibody production) and a cellular immune reaction (antigen-specific CTL induction). Therefore, the oligodeoxynucleotide, complex, and pharmaceutical composition of the present invention, particularly the complex of the present invention and a pharmaceutical composition containing same are useful as vaccine adjuvants.

In the present specification, the adjuvant refers to a pharmaceutic aid that promotes immune responses, which is a substance that non-specifically enhances immune responses to an antigen when administered with the antigen to the living body.

The antigen is not particularly limited as long as it has antigenicity for a mammal (primates such as human and the like, rodents such as mouse and the like, etc.) to be the subject of administration, and can be recognized as an antigen by an antibody or cytotoxic T lymphocyte (CTL, CD8$^+$ T cells). Any substance that becomes an antigen (protein, peptide, nucleic acid, lipid, carbohydrates, and a modification of the aforementioned substance (e.g., modification introduced with deletion, substitution, and/or addition of one or more amino acids (hereinafter mutation etc.) and the like) can be used. As the antigen, antigen derived from pathogen such as protozoa, fungi, bacterium, virus and the like, and an antigen relating to cancer or a particular disease can also be used.

In the present specification, "antigen A derived from a pathogen X" means that antigen A is contained as a constituent factor in the pathogen X. For example, when antigen A is a polypeptide, it means that the amino acid sequence of the polypeptide is present in the amino acid sequence of the protein encoded by the genome of pathogen X.

Examples of the antigen derived from a pathogen include the pathogen itself or a part thereof, an inactivated or attenuated pathogen itself or a part thereof, or a modification introduced with a mutation thereto and the like, and the like.

When an antigen derived from a pathogen is used as the antigen, an immune reaction to the antigen is induced, and a mechanism for immunologically eliminating the pathogen containing the antigen from the body is constructed. Therefore, a composition comprising (a) the oligodeoxynucleotide of the present invention, or the complex of the present invention, and (b) an antigen derived from a pathogen, for inducing an immune reaction to the antigen, is useful for the prophylaxis or treatment of the pathogen.

The complex of the present invention strongly induces both a humoral immune reaction (antigen-specific antibody production), and a cellular immune reaction (antigen-specific CTL induction) to the antigen. Therefore, an antigen derived from an intracellular infectious pathogen (virus, protozoa, fungi, bacterium etc.) known to be recognized by cytotoxic T lymphocytes, an antigen related to cancer cells (e.g., tumor antigen) and the like are preferably used as the antigen.

While the intracellular infectious virus is not particularly limited, examples thereof include RS virus, influenza virus, parainfluenza virus, hepatitis C virus (HCV), hepatitis A virus (HAV), hepatitis B virus (HBV), Ebolavirus, cytomegalovirus, adenovirus, polio virus, Japanese encephalitis virus, measles virus, mumps virus, rubella virus, rabies virus, yellow fever virus, varicella herpes zoster virus, hantavirus, dengue virus, norovirus, rotavirus, parvovirus, corona virus, distemper virus, adult T cell leukemia virus (HTLV-1), human immunodeficiency virus (HIV), herpes virus, papilloma virus and the like. Examples of the intracellular infectious bacteria include *mycoplasma* and the like. Examples of the intracellular infectious protozoa include *plasmodium, schistosoma* and the like. The intracellular infectious pathogen is preferably virus (specifically, RS virus, or influenza virus etc.).

Examples of the antigen related to cancer cells include protein, sugar chain, peptide that are specifically expressed by cancer cells, variant of the aforementioned substances (deleted, substituted, and/or added) or modification thereof and the like.

Since the complex of the present invention strongly induces both the type I and type II interferons, in one embodiment, a virus (e.g., RS virus, influenza virus) that causes acute virus infection, for which both the type I interferon and type II interferon are effective, is selected as the virus.

For example, a composition containing (a) the oligodeoxynucleotide of the present invention, or the complex of the present invention, and (b) an antigen derived from a pathogen or cancer, for inducing an immune reaction to the antigen, is administered to a patient with the pathogen infection or cancer or a human potentially affected with the pathogen infection or cancer, to antigen-specifically activate cytotoxic T lymphocytes (CTLs) in the subject who received the administration, induce the antigen-specific antibody production, i.e., induce a protective immune reaction in the warm-blooded animal (preferably, human), whereby the infection and cancer can be prevented or treated. Accordingly, the composition is useful as a vaccine for the prophylaxis or treatment of the above-mentioned diseases such as infection, cancer and the like.

In addition, since the complex of the present invention can strongly induce both a humoral immune reaction (antigen-specific antibody production) and a cellular immune reaction (antigen-specific CTL induction) to an antigen, any of a surface antigen and an internal antigen of pathogen and cancer cell can be used as the antigen, and use of a mixture of a surface antigen and an internal antigen is also desirable.

A composition comprising (a) the oligodeoxynucleotide of the present invention, or the complex of the present invention, and (b) an antigen, for inducing an immune reaction to the antigen, can be prepared according to the above-mentioned pharmaceutical composition of the present invention.

The contents disclosed in any publication cited in the present specification, including patents and patent applications, are hereby incorporated in their entireties by reference, to the extent that they have been disclosed herein.

EXAMPLES

The present invention is explained in more detail in the following by referring to Examples, which are not to be construed as limitative.
[Method]
Animals and Reagents Generation of Tlr9-deficient and Dectin-1-deficient mice have been described in (Koyama, S., et al., Science translational medicine 2, 25ra24 (2010); Saijo, S., et al., Nature immunology 8, 39-46 (2007)). C57BL/6J mice were purchased from NIHON CLEA. All animal experiments were conducted in accordance with the institutional guidelines for the National Institute of Biomedical Innovation, and for the Osaka University animal facility. The following CpG ODNs were synthesized by GeneDesign, Inc.
(underline indicates phosphorothioate bonds).

TABLE 1

K3 (5'-<u>ATC GAC TCT CGA GCG TTC TC</u>-3') (SEQ ID NO: 1);

K3-dA₄₀ (5'-<u>ATC GAC TCT CGA GCG TTC TC</u>-40mer <u>A</u>-3') (SEQ ID NO: 2);

dA₄₀-K3 (5'-40mer <u>A</u>-<u>ATC GAC TCT CGA GCG TTC TC</u>-3') (SEQ ID NO: 3);

D35 (5'-<u>G</u>GT GCA TCG ATG CAG GG<u>G GG</u>-3') (SEQ ID NO: 4);

CpG21798 (5'-<u>TCG TCG ACG ATC GGC GCG CGC CG</u>-3') (SEQ ID NO: 5);

CpG21889 (5'-<u>TCG TCG ACG ATC GGC GCG CGC CG</u>-3') (SEQ ID NO: 6);

CpG2395 (5'-<u>TCG TCG TTT TCG GCG CGC GCC G</u>-3') (SEQ ID NO: 7);

M362 (5'-<u>TCG TCG TCG TTC GAA CGA CGT TGA T</u>-3') (SEQ ID NO: 8);

Alexa 488-labeled K3;

Alexa 488-labeled K3-dA40;

Alexa 647-labeled K3;

Alexa 647-labeled K3-dA40

Particularly, the synthesis of K3-dA35 (SEQ ID NO: 12), K3-dA30 (SEQ ID NO: 11), K3-dA25 (SEQ ID NO: 10) and K3-dA20 (SEQ ID NO: 9), in addition to the above-mentioned K3-dA40 (SEQ ID NO: 2), is described (Table 2).

TABLE 2

K3-dA40:
<u>AsTsCsGsAsCsTsCsTsCsGsAsGsCsGsTsTsCsTsCsAsAsAsAsAs
AsAsAsAsAsAsAsAsAsAsAsAsAsAsAsAsAsAsAsAsAsAsAsAsAs
AsAsAsAsAsAsAsA</u> (Sequence Listing, SEQ ID NO: 2)

K3-dA35:
<u>AsTsCsGsAsCsTsCsTsCsGsAsGsCsGsTsTsCsTsCsAsAsAsAsAs
AsAsAsAsAsAsAsAsAsAsAsAsAsAsAsAsAsAsAsAsAsAsAsAsAs
AsAsAsAsA</u> (Sequence Listing, SEQ ID NO: 12)

TABLE 2-continued

K3-dA30:
<u>AsTsCsGsAsCsTsCsTsCsGsAsGsCsGsTsTsCsTsCsAsAsAsAsAs
AsAsAsAsAsAsAsAsAsAsAsAsAsAsAsAsAsAsAsAsAsAsAsA</u>
(Sequence Listing, SEQ ID NO: 11)

K3-dA25:
<u>AsTsCsGsAsCsTsCsTsCsGsAsGsCsGsTsTsCsTsCsAsAsAsAsAs
AsAsAsAsAsAsAsAsAsAsAsAsAsAsAsAsAsA</u> (Sequence
Listing, SEQ ID NO: 10)

K3-dA20:
<u>AsTsCsGsAsCsTsCsTsCsGsAsGsCsGsTsTsCsTsCsAsAsAsAsAs
AsAsAsAsAsAsAsAsAsAsAsA</u> (Sequence Listing,
SEQ ID NO: 9)

(In the above-mentioned sequences, s shows that the phosphodiester bond between nucleosides is substituted by a phosphorothioate bond.)

The oligodeoxynucleotides were synthesized by a conventional method, solid phase phosphoramidite method (Nucleic Acids in Chemistry and Biology, 3. Chemical synthesis (1990) ed. G. Michael Blackburn and Michael J. Gait. Oxford University Press).

Table 3 shows the molecular weight of CpG ODNs described in Table 2, and retention time analyzed by reversed-phase HPLC under the following conditions (column: Waters, X-Bridge C18 2.5 μm, 4.6×75 mm, solution A: 100 mM hexafluoroisopropanol, 8 mM triethylamine, solution B: methanol, B %:5%→30% (20 min, linear gradient); 60° C.; 1 ml/min; 260 nm).

TABLE 3

| compound | Calculated value | measured value | retention time (min) |
|---|---|---|---|
| K3-dA40 | 19520.3 | 19519.0 | 14.9 |
| K3-dA35 | 17873.9 | 17872.8 | 15.0 |
| K3-dA30 | 16227.5 | 16225.7 | 14.9 |
| K3-dA25 | 14581.1 | 14580.5 | 14.7 |
| K3-dA20 | 12934.8 | 12933.3 | 14.6 |

Ovalbumin (OVA) was purchased from Seikagaku Kogyo. DQ-OVA, Alexa488-OVA, CFSE, and Lipofectamine 2000 were purchased from Invitrogen. Hoechst33258, Zymosan, and Curdlan were purchased from SIGMA. Zymosan-Depleted was purchased from Invivogen. Clodronate liposome was purchased from FormuMax. Influenza split product vaccine, formalin-inactivated whole-virus (WIV), and purified influenza viruses (H1N1) were prepared as previously described (Koyama, S., et al., Science translational medicine 2, 25ra24 (2010)).
Complexation of CpG ODN and SPG (FIG. 1)

7.22 mg of K3-dA40 was dissolved in water (3.7 mL). SPG (15 mg, Mitsui Sugar Co., Ltd.) was dissolved in 0.25 N NaOH (1 mL). A 1 mL volume of 330 mM NaH₂PO₄ was added to the DNA solution, then the SPG solution was added to the DNA/NaH₂PO₄ solution and kept at 4° C. overnight to complete the complexation. The molar ratio (MSPG/MDNA) was fixed at 0.27. Formation of the complex was confirmed by a microchip electrophoresis apparatus (SHIMADZU: MultiNA).
Complexation of CpG ODN and LNT (FIG. 1)

Lentinan (LNT: Ajinomoto Co., Inc., lot No.: 2D8X1) was dissolved in 0.25N NaOH to 50 mg/ml, and the mixture was left standing at room temperature overnight. Various CpG ODNs (Tables 2, 3) were dissolved in water for injection to 100 mM. LNT aqueous solution and various CpG aqueous solutions (K3-dA20 (SEQ ID NO: 9), K3-dA25 (SEQ ID NO: 10), K3-dA30 (SEQ ID NO: 11), K3-dA35 (SEQ ID NO: 12), K3-dA40 (SEQ ID NO: 2)) were mixed at the ratios shown in Table 4, then the same volume of 330 mM $NaH_2PO_4$ as LNT was added, and the mixture was maintained at 4° C. overnight to complete the complexation. Formation of the complex was confirmed by shift of CpG ODN to the higher molecular weight side by size-exclusion chromatography, while monitoring the absorption at 260 nm. (System: Agilent 1100 series, Column: Asahipak GF7 M-HQ (Shodex), two columns connected, Flow rate: 0.8 mL/min, Buffer: 10 mM EDTA PBS, pH 7.4, Temperature: 40° C.)

TABLE 4

| CpG-LNT | CpG ODN type | (µg) | LNT (µg) | |
|---|---|---|---|---|
| K3-dA20-LNT | K3-dA20 | 69 | 113 | |
| K3-dA20-LNT | K3-dA20 | 138 | 136 | |
| K3-dA25-LNT | K3-dA25 | 78 | 85 | |
| K3-dA30-LNT #1 | K3-dA30 | 433 | 425 | results 9) |
| K3-dA30-LNT #2 | K3-dA30 | 433 | 510 | results 9), 10), 11) |
| K3-dA35-LNT #1 | K3-dA35 | 477 | 496 | results 9) |
| K3-dA35-LNT #2 | K3-dA35 | 477 | 595 | results 9), 10), 11) |
| K3-dA40-LNT #1 | K3-dA40 | 521 | 567 | results 9) |
| K3-dA40-LNT #2 | K3-dA40 | 521 | 680 | results 9), 10), 11) |
| K3-dA35-LNT | K3-dA35 | 1527 | 1524 | results 12) |
| K3-dA40-LNT | K3-dA40 | 1667 | 1741 | results 12) |

Preparation and Stimulation of Human PBMCs (FIGS. 2, 3, 6 and 7)

PBMCs were obtained from three healthy adult male volunteers (30-40-years-old). All experiments using human PBMCs were approved by Institutional Review Board of the National Institute of Biomedical Innovation. After preparation of PBMCs using Ficoll, they were plated at a concentration of $1 \times 10^7$ cells/mL. PBMCs were maintained in complete RPMI (RPMI 1640 supplemented with 10% FCS, penicillin, and streptomycin). PBMCs were stimulated with K3 (0.24, 0.74, 2.2, 6.6, 20 µg/mL), K3-dA40, K3-SPG (complex of K3-dA40), dA40-K3, SPG-K3 (complex of dA40-K3), D35, CpG21798, CpG21889, CpG2395, or M362 for 24 h. Supernatants were subjected to ELISA for pan-IFN-α (Mabtech), IL-6 (R&D), and Milliplex (Millipore).

Figure 4:
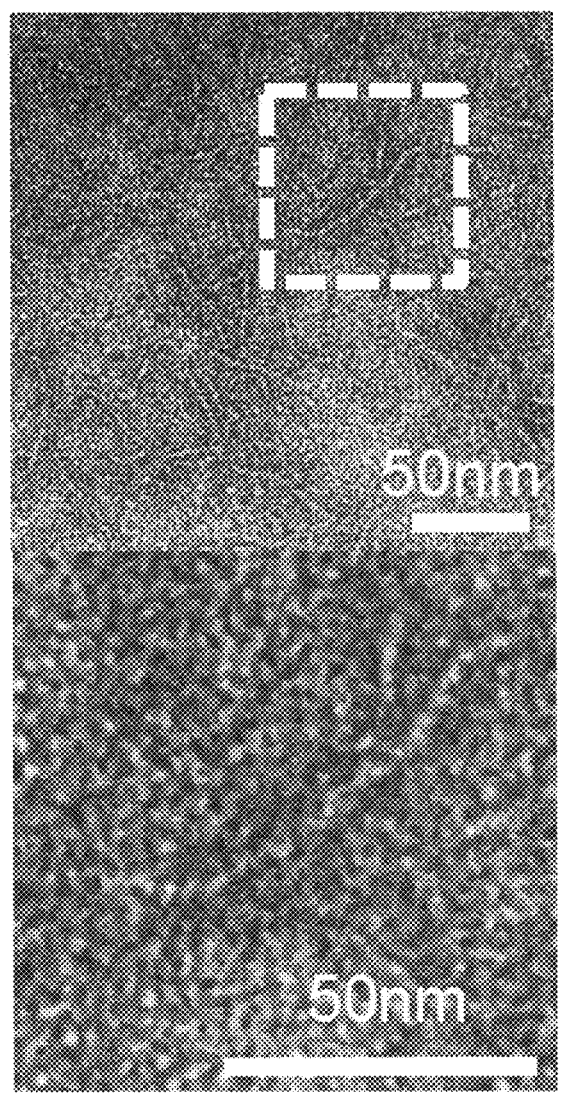
FIG. 4 shows a scanning electron microscopic image of K3-SPG.

Electron Microscopy Analysis (FIG. 4)

Before staining, samples were dropped on formvar-carbon-coated grids. For negative staining, a drop of 2% uranyl acetate (pH 4.0) was placed on the grip and left to air dry. The grips were examined at a magnification of ×40,000 on an electron microscope (Hitachi H-7650).

Figure 5:
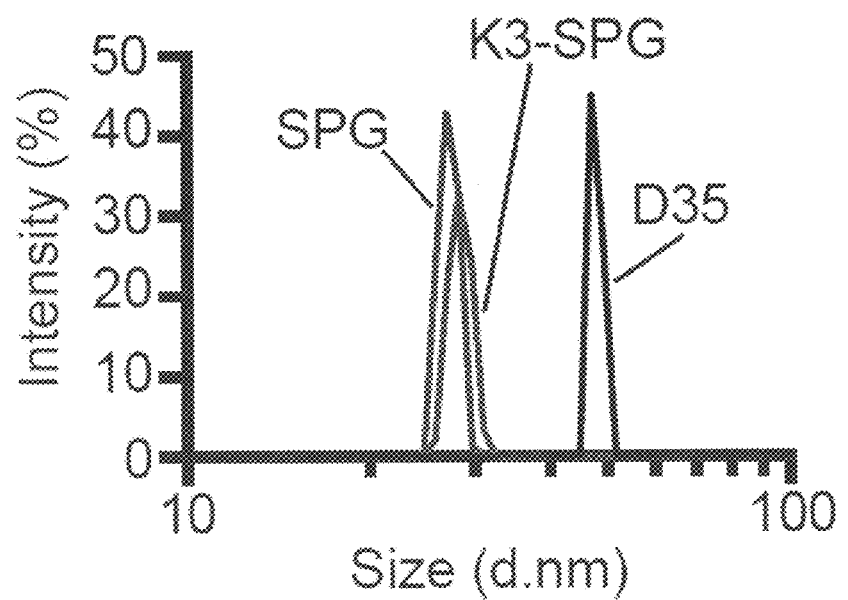
FIG. 5 shows the particles sizes of K3-SPG, SPG and D35 as analyzed by dynamic light scattering.
Figure 6:
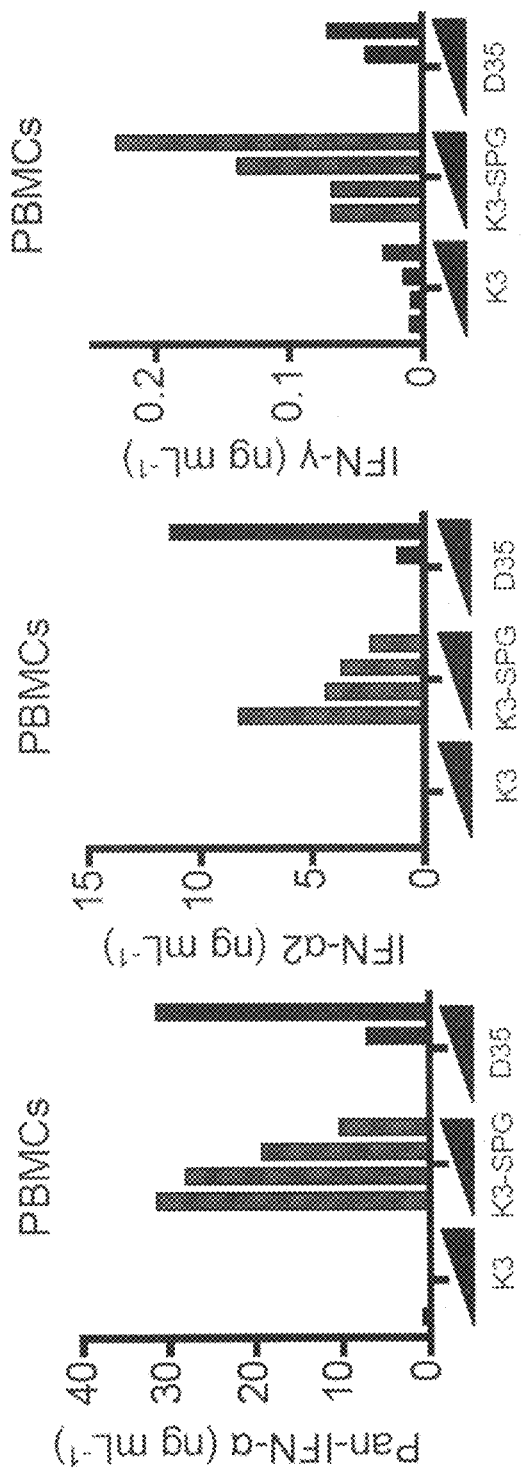
FIG. 6 shows the production of pan-IFN-α, IFN-α2, and IFN-γ by PBMCs induced by stimulation with K3, K3-SPG or D35.

Dynamic Light Scattering (FIG. 5)

Mean nano-particle sizes in an aqueous solution at 80° C. were measured using dynamic light scattering on a Malvern Instruments Zeta Sizer.

Figure 8:
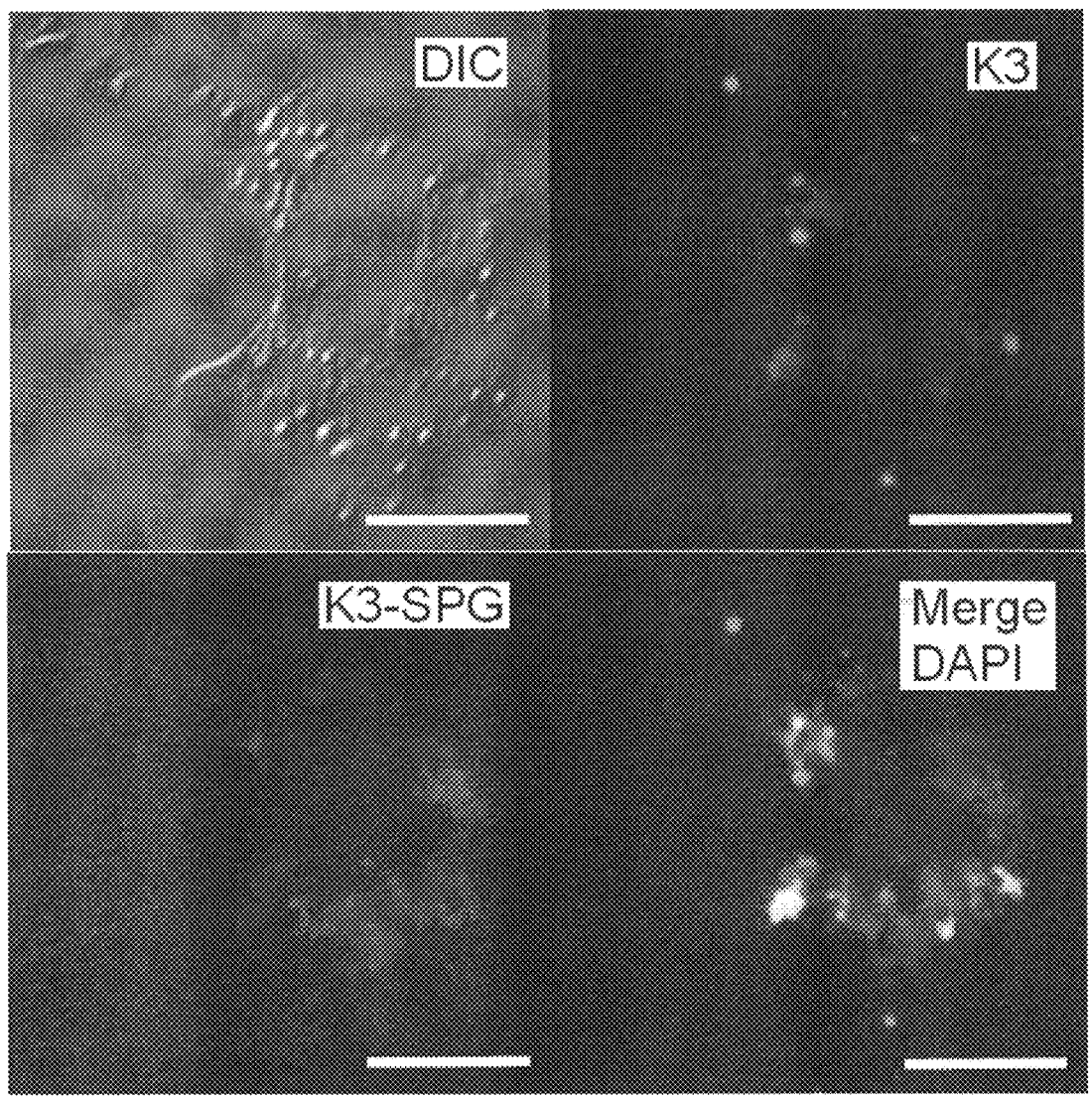
FIG. 8 shows colocalization of K3-SPG with K type CpG ODN-containing endosome. The scale bar shows 10 μm. The results are representative of at least two independent experiments.
Figure 9:
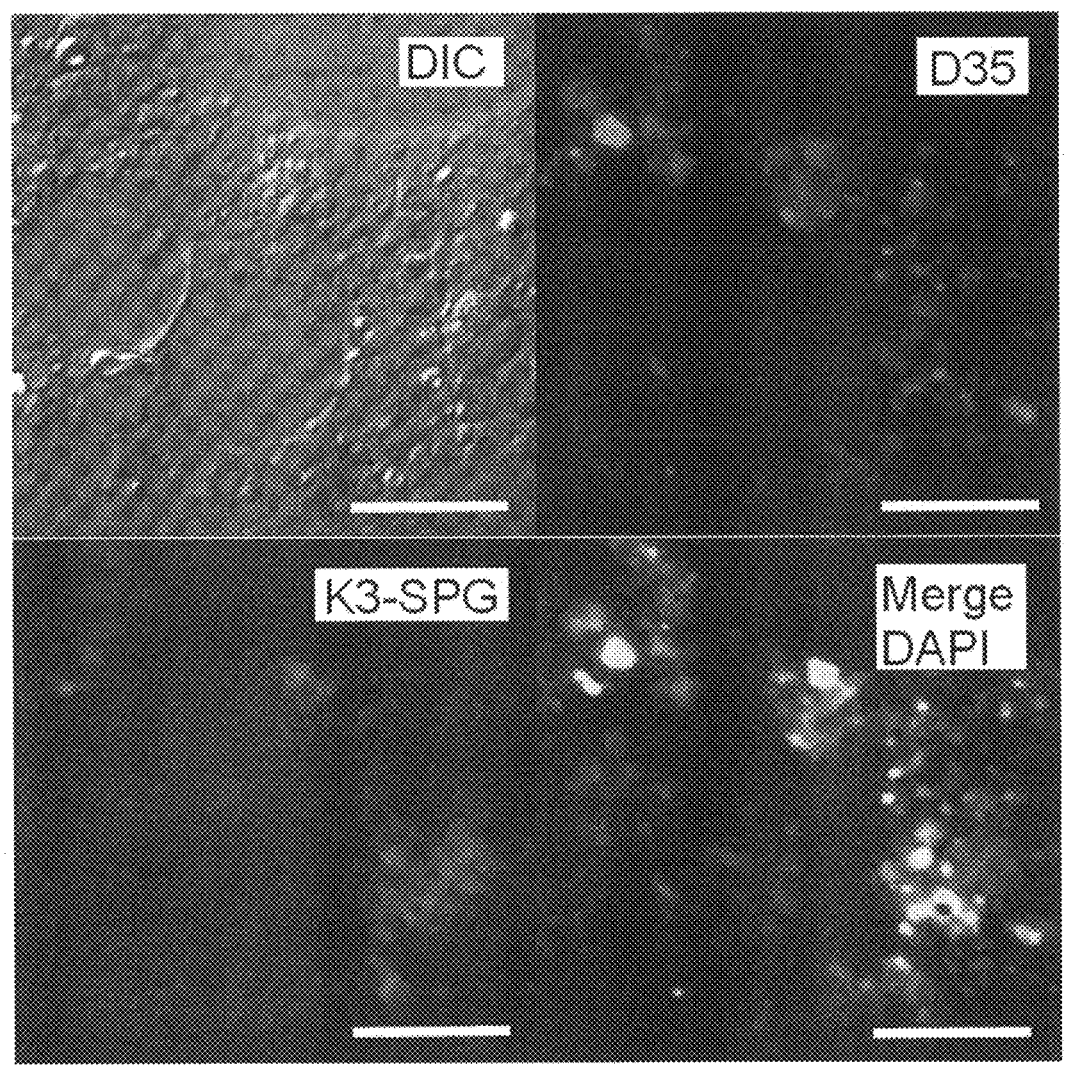
FIG. 9 shows colocalization of K3-SPG with D type CpG ODN-containing endosome. The scale bar shows 10 μm.
Figure 10:
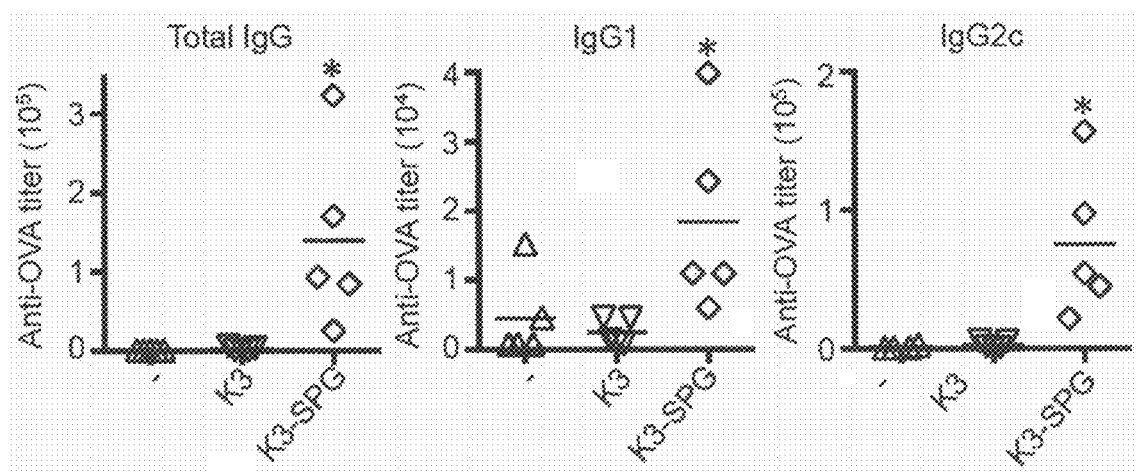
FIG. 10 shows antigen specific serum antibody titers of mice immunized with OVA alone, OVA+K3, or OVA+K3-SPG. *$p<0.05$ (Mann-Whitney U test).

Splenocyte and Dendritic Cell Cultures (FIGS. 8 and 9)

Mouse spleens were collected from 6-week-old C57BL/6J, Tlr9-deficient, and Dectin-1-deficient mice. After suspension of splenocytes, red blood cells (RBCs) were lysed with ACK lysis buffer and cells were maintained in complete RPMI. Cells were plated at $1 \times 10^7$ cells/mL. Bone marrow-derived DCs were generated by culturing for 7 days with human Flt3L (Peprotech) (100 ng/mL). Cells were plated at a concentration of $1 \times 10^7$ cells/mL. BMDMs were generated by culturing for 7 days with mouse M-CSF (Peprotech) (20 ng/mL). These cells were maintained in complete RPMI.

Intracellular Distribution (FIGS. 8 and 9)

BMDMs were plated at $5 \times 10^7$ cells/mL and stimulated with Alexa 488-K3 (1 µM) plus Alexa 647-K3-SPG (1 µM), or Alexa 488-D35 (1 µM) plus Alexa 647-K3-SPG (1 µM) for 3 h. Cells were stained with Hoechst33258 for 30 min to visualize nuclei, then cells were fixed and analyzed using fluorescence microscopy.

Immunization

Figure 13:
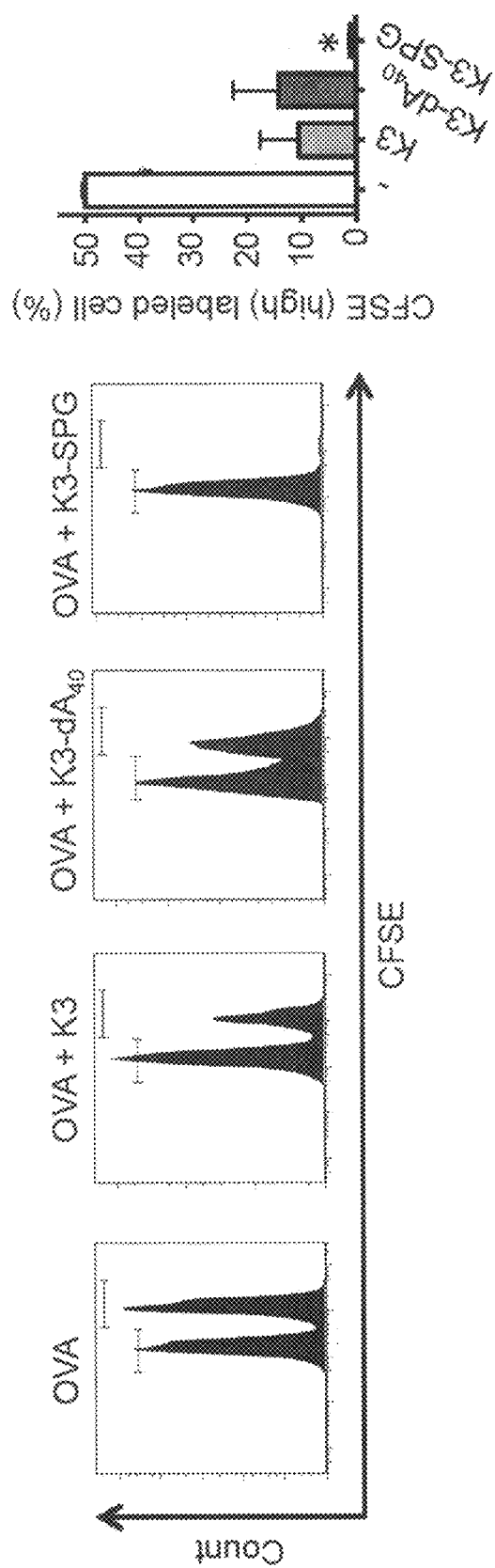
FIG. 13 shows in vivo OVA-specific CTL activity induced by immunization with OVA alone, OVA+K3, OVA+K3-dA40 or OVA+K3-SPG. *$p<0.05$ (Mann-Whitney U test).

Six-week-old C57BL/6J, Tlr9-deficient, and Dectin-1-deficient mice were administered with
OVA (0.1, 1, 10, or 100 µg);
OVA (0.37, 1.1, 3.3, or 10 µg) and K3(538 pmol);
OVA (0.37, 1.1, 3.3, or 10 µg) and K3-dA40 (538 pmol); or
OVA (0.37, 1.1, 3.3, or 10 µg) and K3-SPG (538 pmol)
at the base of the tail at days 0 and 10. For other experiments, 6-week-old C57BL/6J mice were administered with split vaccine (0.1 µg) alone;
split vaccine plus K3 (538 pmol); or
split vaccine plus K3-SPG (538 pmol)
at days 0 and 10 at the base of the tail. Blood was drawn at day 17 and antigen-specific serum antibody titers were measured by ELISA (FIGS. 10, 15a, 16, 25, 28a, 29 and 43a). Mouse spleens were collected at day 17 and splenocytes prepared by mentioned above method. Cells were re-stimulated with
OVA257-264 (OVA257):SIINFEKL (10 µg/mL);
OVA323-339 (OVA323):ISQAVHAAHAEINEAGR (10 µg/mL);
Whole OVA protein (OVA) (10 µg/mL);
NP260-283 (NP260):ARSALILRGSVAHKSCLPACVYGP (10 µg/mL); or
split vaccine (10 µg/mL)
for 24 or 48 h. The supernatants were subjected to ELISA for mouse IFN-γ (FIGS. 11, 15b, 17, 26, 28b, 30 and 43b). For the tetramer assay, splenocytes were stained with the H-2Kb OVA tetramer (MBL), anti-CD8a (KT15), anti-TCRβ (H57-597), anti-CD62L (MEL-14), and anti-CD44 (IM7) antibodies, and 7-AAD. OVA tetramer$^+$ CD44$^+$ CD8α$^+$ TCRβ$^+$ cell numbers were determined by FACS (FIGS. 12, 15c, 27, 28c and 31).

in vitro CTL assay (FIG. 13)

Six-week-old C57BL/6J mice were administered with
OVA (100 µg);
OVA plus K3 (3.3 µg);
OVA plus K3-dA40 (3.3 µg); or
OVA with K3-SPG (3.3 µg)
at the base of the tail at day 0. At 7 days post-immunization, naïve C57BL/6J splenocytes were labeled with different concentration of CFSE (5 or 0.5 µM) for 10 min at 37° C. The stained cells at high concentrations were pulsed with OVA257 (10 µg/mL) for 90 min at 37° C. After washing twice with medium, labeled cells were mixed and transferred to immunized mice by intravenous administration. Twenty-four hours after the transfer, splenocytes were collected and the percentage of CFSE-labeled cells was measured by FACS.

Peptide Immunization

Figure 14:
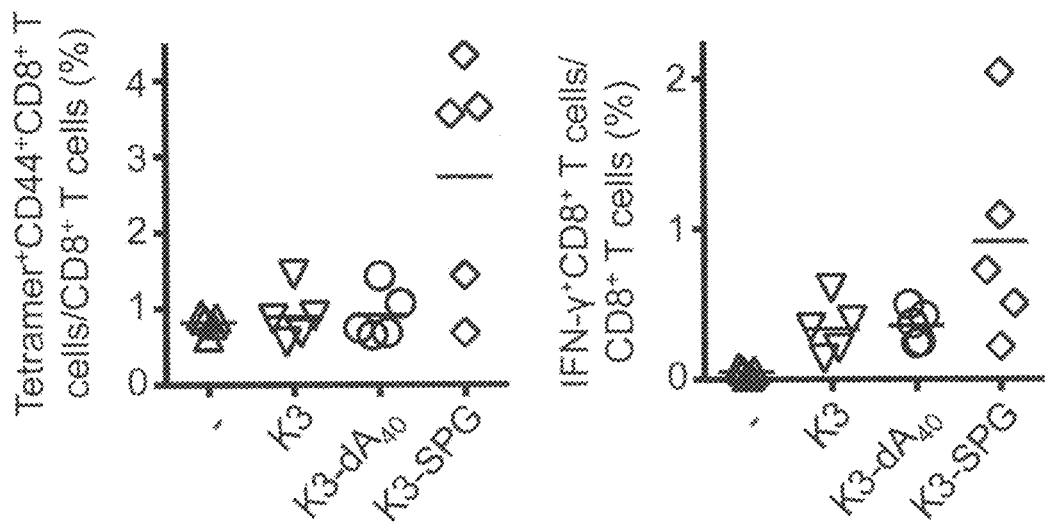
FIG. 14 shows a peptide vaccine adjuvant effect of K3-SPG.

C57BL/6J mice were immunized with
OVA257 (10 µg);
OVA257 plus K3 (10 µg);
OVA257 plus K3-dA40 (10 µg); or
OVA257 plus K3-SPG (10 µg).
Seven days after immunization, splenocytes were prepared and stained with the H-2Kb OVA tetramer, anti-CD8α, anti-TCRβ, anti-CD62L, and anti-CD44 antibodies. OVA tetramer$^+$ CD44$^+$ CD8α$^+$ TCRβ$^+$ cell numbers were analyzed by FACS (FIG. 14 left). Prepared splenocytes were re-stimulated in vitro with OVA257 (10 µg/mL) plus Golgi Plug for 4 h. Cells were stained with anti-IFN-γ, anti-CD8α, and anti-CD3e antibodies, and IFN-γ+CD8α+ CD3e+ cell numbers were determined by FACS (FIG. 14 right).

Figure 18:
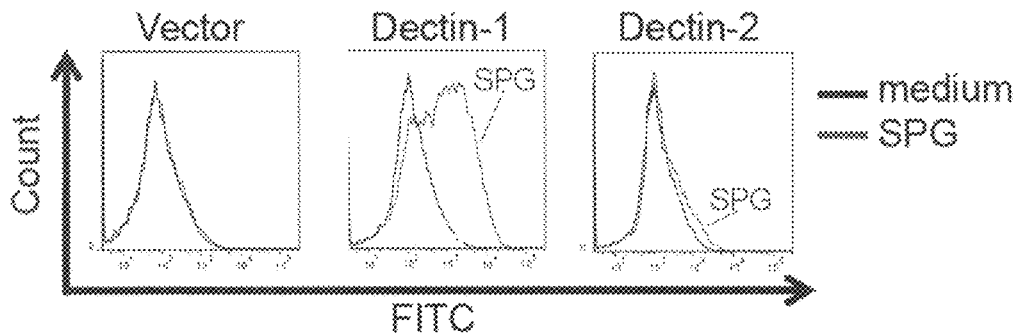
FIG. 18 shows binding of SPG to empty (vector), Dectin-1, or Dectin-2 transfectant.
Figure 19:
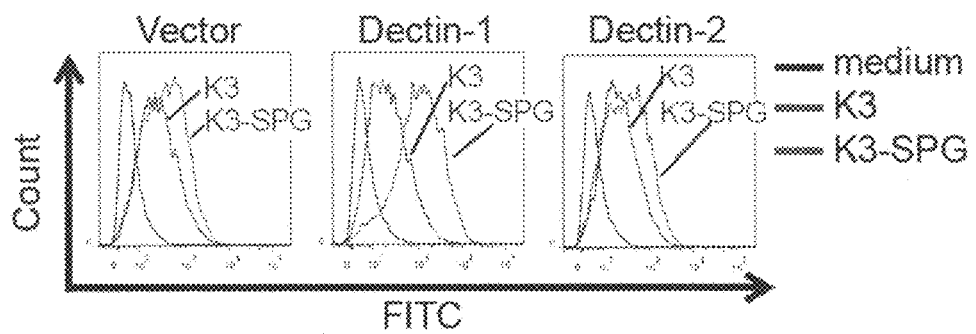
FIG. 19 shows binding of K3 or K3-SPG to empty (vector), Dectin-1, or Dectin-2 transfectant.
Figure 20:
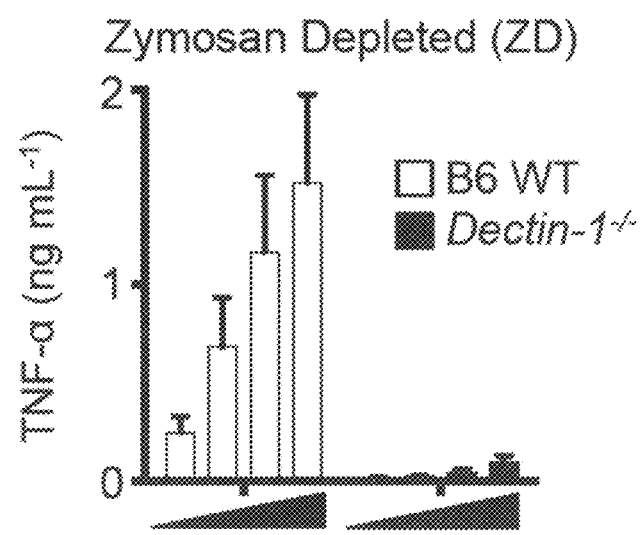
FIG. 20 shows TNF-α production by splenocytes of C57BL/6J mouse or Dectin-1 deficient mouse, which was induced by Zymosan Depleted stimulation.

Transfection and Dectin-1 Binding Assay (FIGS. 18 and 19)

HEK293 cells were transfected with empty, Dectin-1, or Dectin-2 expression plasmids using Lipofectamine 2000. At 48 h post-transfection, cells were treated with FITC-SPG (0.5 µM), Alexa 488-labeled K3-dA40 (0.5 µM), or Alexa 488-labeled K3-SPG (0.5 µM) for 60 min at 37° C. After treatment, cells were harvested and SPG or CpG ODN-positive cells were analyzed by FACS.

Stimulation of Immune Cells (FIGS. 20, 21, 22, 23 and 24)

Splenocytes and FL-DCs from C57BL/6J, Tlr9-deficient, or Dectin-1-deficient mice were stimulated with K3-SPG (0.014, 0.03, 0.04, 0.08, 0.12, 0.25, 0.37, 0.74, 1.1, 2.2, 3.3, 6.7, 10, or 20 µg/mL), Zymosan (3.7, 11.1, 33.3, or 100 µg/mL), Curdlan, Zymosan-Depleted, or SPG for 24 h. In other experiments, splenocytes from C57BL/6J or Dectin-1-deficient mice were stimulated with Zymosan-Depleted (100, 33.3, or 11.1 µg/mL) or SPG (100, 33.3, or 11.1 µg/mL), with or without D35 (1 µM) for 24 h. Supernatants were subjected to ELISA for IFN-α (PBL), IL-6 (R&D), IL-12 p40 (R&D), IL-12 p70 (R&D), and Bioplex (BIO-RAD).

Figure 32:
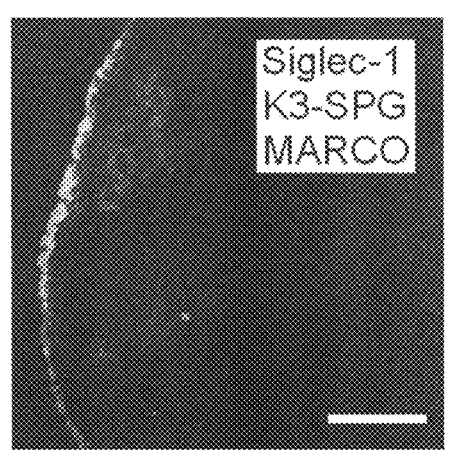
FIG. 32 shows localization of K3-SPG on the iLNs surface at 1 hr after administration of Alexa 488-K3-SPG.

Immunohistochemistry (FIG. 32)

C57BL/6J mice were administered with
DQ-OVA (10 µg);
Alexa 488-K3-SPG (10 µg);
Alexa 647-K3-SPG (10 µg); or
DQ-OVA plus Alexa647-K3-SPG (10 µg)
at the base of the tail. After collection of iLNs, the frozen sections were prepared using a cryostat. Frozen sections were fixed with 4% paraformaldehyde for 10 min and incubated with anti-Siglec-1 (MOMA-1), anti-MARCO (ED31), anti-CD3e (145-2C11), or anti-CD11c (N418) antibodies. Imaging results were analyzed by ImageJ.

Figure 33:
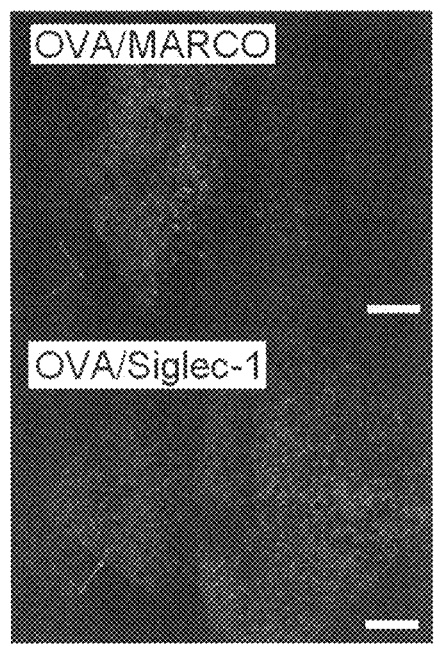
FIG. 33 shows localization of OVA, MARCO$^+$ cells, and Siglec-1$^+$ cells in iLNs at 1 hr after administration of DQ-OVA.
Figure 35:
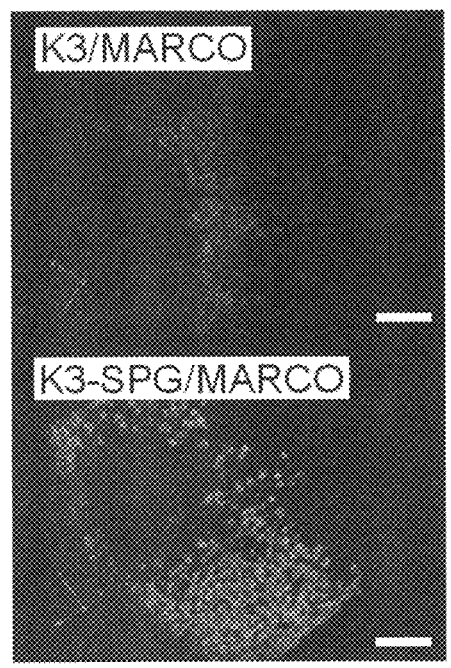
FIG. 35 shows localization of K3, K3-SPG, and MARCO$^+$ cells in iLNs at 1 hr after administration of Alexa 488-K3 or Alexa 488-K3-SPG.

Two-Photon Microscopy (FIGS. 33 and 35)

C57BL/6J, Tlr9-deficient, or Dectin-1-deficient mice were administered with DQ-OVA (10 µg), Alexa 488-K3 (10 µg), or Alexa 488-K3-SPG (10 µg) at the base of the tail. At 30 min prior to iLN collection, mice were administered with anti-PE-MARCO, or anti-PE-Siglec-1 antibodies at the base of the tail. At 1 h post-administration of antigen or adjuvant, iLNs were collected and prepared for imaging analysis using a two-photon microscope (Olympus). Pearson's correlation was calculated using Volocity co-localization analysis.

Figure 34:
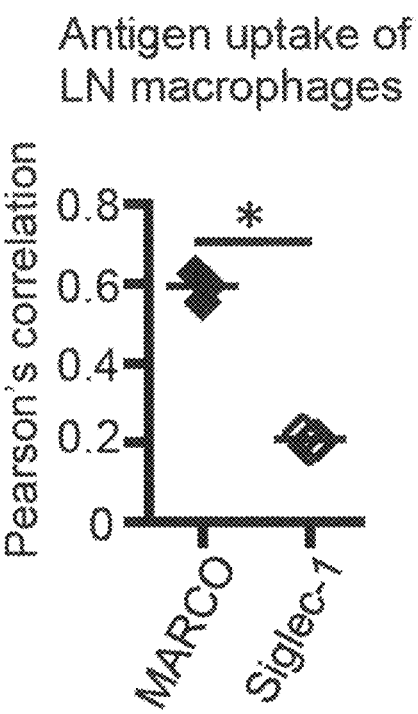
FIG. 34 shows the results of analysis, by Volocity, of colocalization of OVA with MARCO$^+$ cells or Siglec-1$^+$ cells in FIG. 33. *p<0.05 (t-test).
Figure 36:
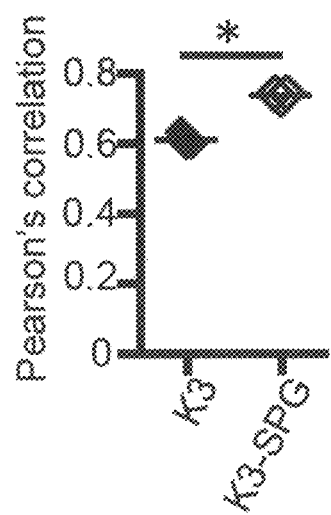
FIG. 36 shows the results of analysis, by Volocity, of colocalization of K3 or K3-SPG with MARCO$^+$ cells in FIG. 35. *p<0.05 (t-test).

In Vivo Distribution of Antigen and Adjuvant (FIGS. 34 and 36)

C57BL/6J mice were administered with
Alexa 647-K3 (538 pmol);
Alexa 647-K3-SPG (538 pmol);
Alexa 488-OVA (10 µg);
Alexa 488-OVA plus K3 (10 µg);
Alexa 488-OVA plus K3-SPG (10 µg);
DQ-OVA (10 µg);
DQ-OVA plus Alexa 647-K3 (538 pmol); or
DQ-OVA plus Alexa 647-K3-SPG (538 pmol)
at the base of the tail. Twenty-four hours after administration, iLNs were collected. To prepare single cell suspensions, iLNs were incubated with collagenase D (1 mg/mL) and DNase I (0.1 mg/mL) for 30 min at 37° C. Prepared cells were incubated with anti-B220 (RA3-6B2), anti-CD8a (56-6.7), and anti-CD11c antibodies to separate the different DC populations. Cellular uptake of OVA and CpG ODNs were analyzed by FACS.

Figure 37:
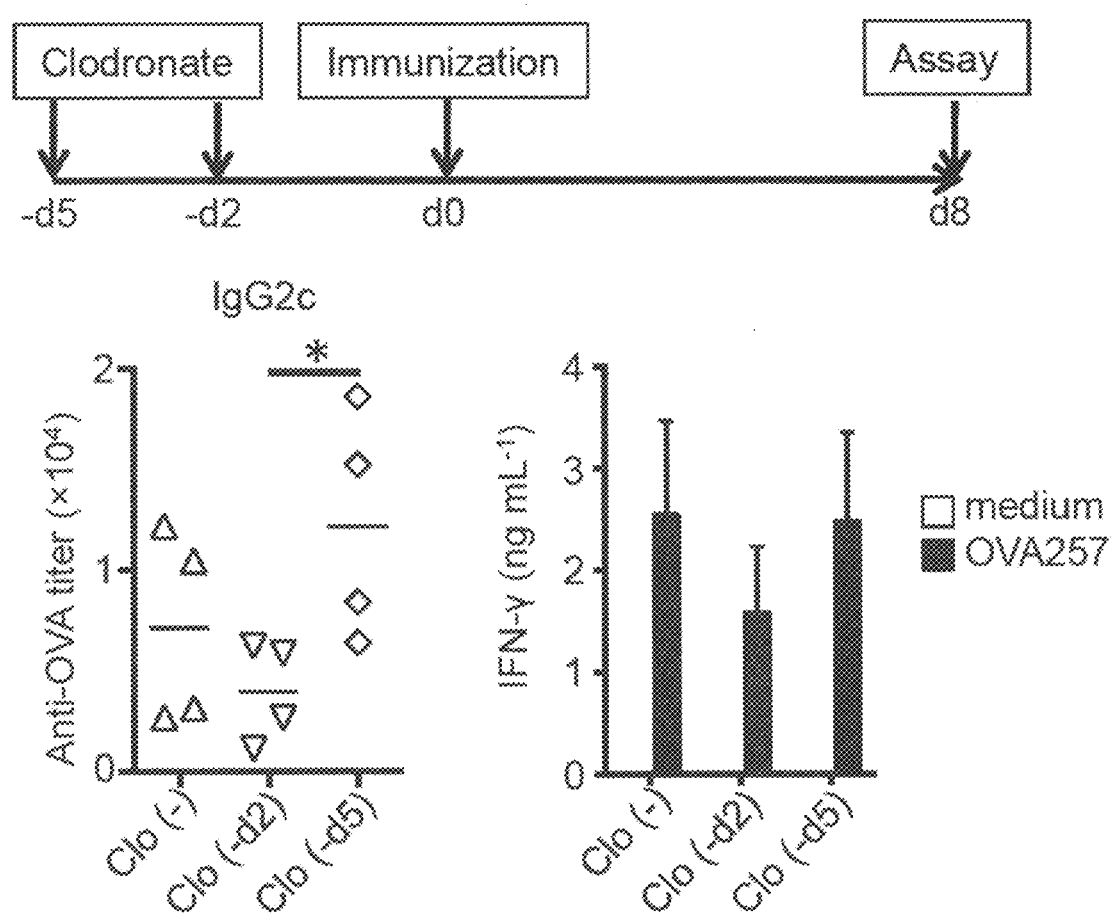
FIG. 37 shows the protocol of depletion experiment with clodronate liposome (upper panel), antigen specific antibody titer in the serum (lower left), and cytokine production by antigen-stimulation. *p<0.05 (t-test).

Clodronate Liposome Injection (FIG. 37)

Six-week-old C57BL/6J mice were administered clodronate liposome at the base of the tail either five or two days prior to immunization. Mice were immunized at the base of the tail with OVA plus K3-SPG on day 0. Blood and spleen were collected at day 8, and serum antibody titers and T cell responses were measured by ELISA.

Figure 38:
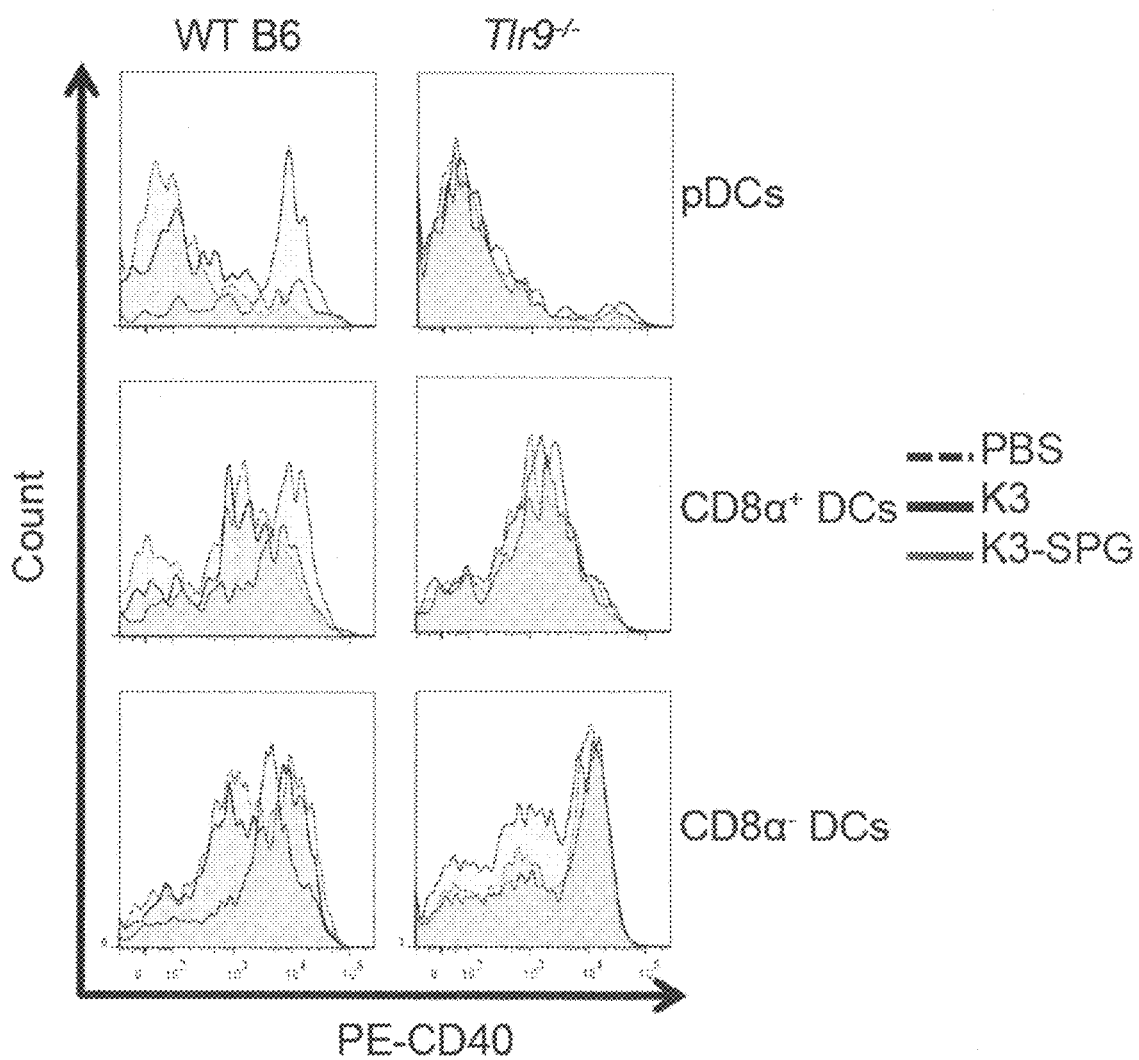
FIG. 38 shows CD40 expression in various DCs of C57BL/6J or Tlr9−/− mice administered with K3 or K3-SPG.

Investigation of In Vivo DC Activation (FIG. 38)

C57BL/6J or Tlr9-deficient mice were administered with K3 (10 µg) or K3-SPG (10 µg) to the base of the tail. At 24 h after administration, iLNs were prepared by the methods mentioned above. Cells were incubated with anti-CD11c, -mPDCA-1 (JF05-1C2.4.1), -CD8α, and -CD40 (3/23) antibodies, then analyzed by FACS.

Investigation of Defense Response Against Infection of Influenza Virus

Figure 39:
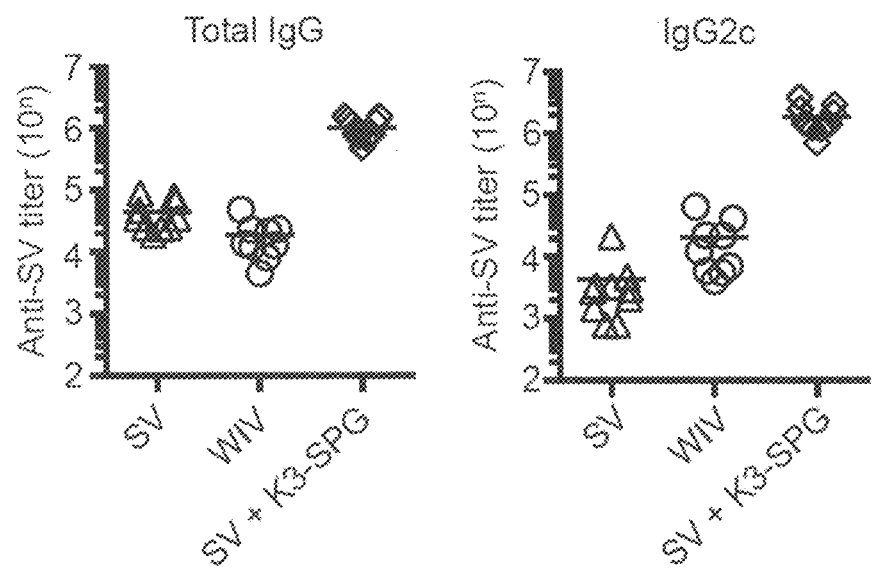
FIG. 39 shows antigen specific antibody titer in the serum in mice immunized with SV, WIV or SV+K3-SPG.
Figure 40:
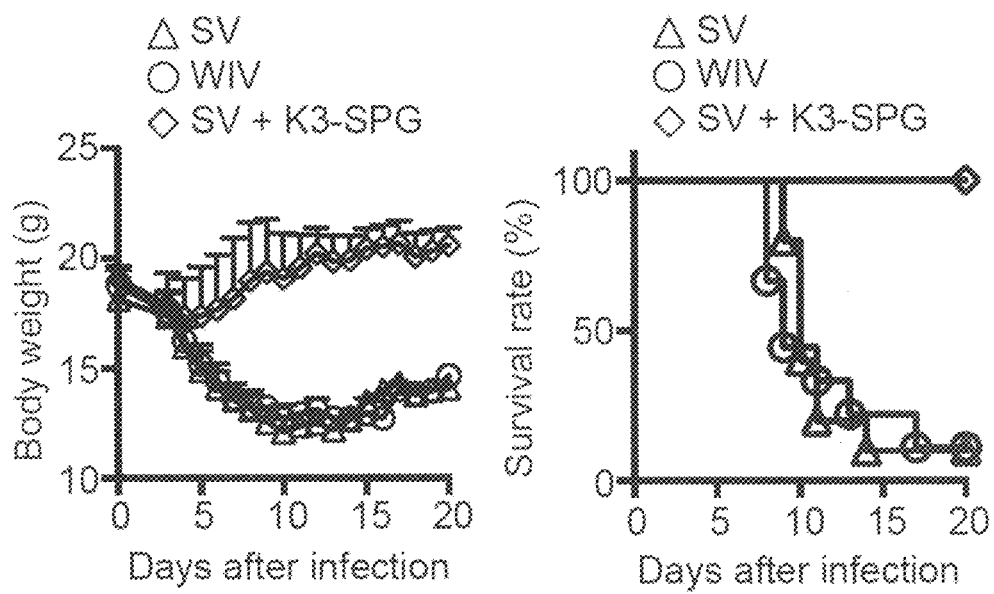
FIG. 40 shows time-course changes of body weight (left) and survival curve (right) when immunized with SV, WIV or SV+K3-SPG, followed by challenge with influenza virus A/P/R8(H1N1).

Six-week-old C57BL/6J mice were administered with
split vaccine (0.1 µg);
split vaccine plus K3-SPG (10 µg); or
WIV (0.2 µg)
at days 0 and 14. Two weeks after immunization, serum antibody titers were measured by ELISA (FIG. 39) and mice were challenged intranasally with $2.3 \times 10^3$ pfu (10 $LD_{50}$) of influenza virus A/PR/8/34. Changes in body weight and mortality of challenged mice were monitored for 20 days (FIG. 40).

Figure 41:
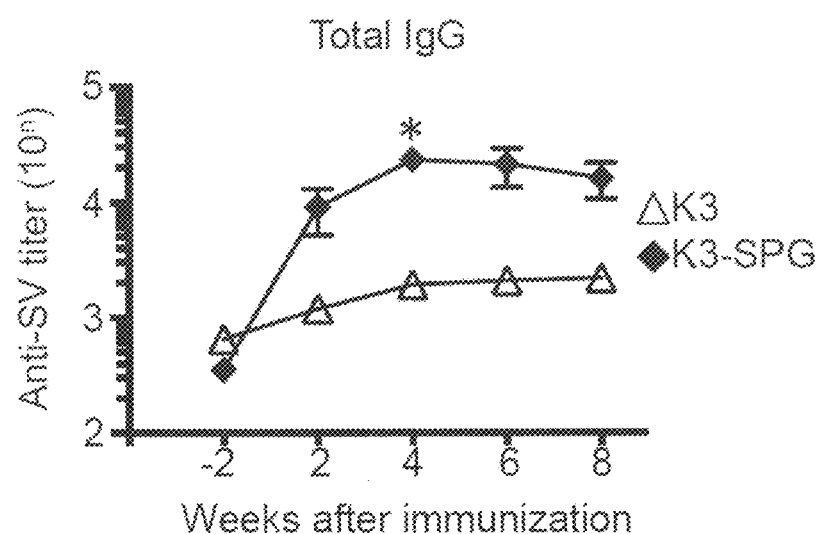
FIG. 41 shows time-course changes of antigen specific serum antibody titer in the serum of *Macaca fascicularis* immunized with SV+K3 or SV+K3-SPG. *p<0.05 (t-test).
Figure 42:
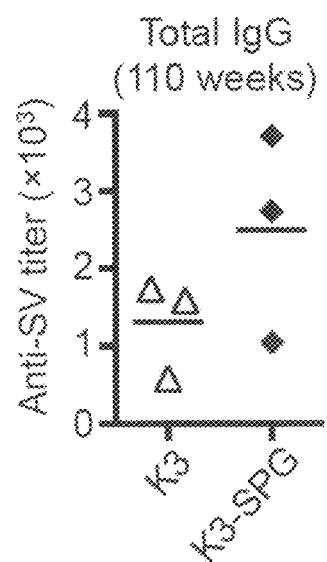
FIG. 42 shows antigen specific serum antibody titer in the serum of *Macaca fascicularis* immunized with SV+K3 or SV+K3-SPG (on week 110).

Vaccine model of cynomolgus monkey (FIGS. 41 and 42)

Cynomolgus monkeys were subcutaneously administered with influenza split vaccine (5 µg) plus K3 (5 nmol), or split vaccine and K3-SPG (5 nmol) at days 0 and 14. Blood samples were collected at −2, 2, 4, 6, 8, and 110 weeks, and serum antibody titers were measured by ELISA.

Statistical Analysis

Stastical significance (P<0.05) between groups was determined using the Student's t test or Mann-Whitney U test.

[Results]

1) A Rod-Shape Nano-Size Particle of K3-SPG Gains Dual Characteristics of K and D Type CpG ODN.

Figure 2:
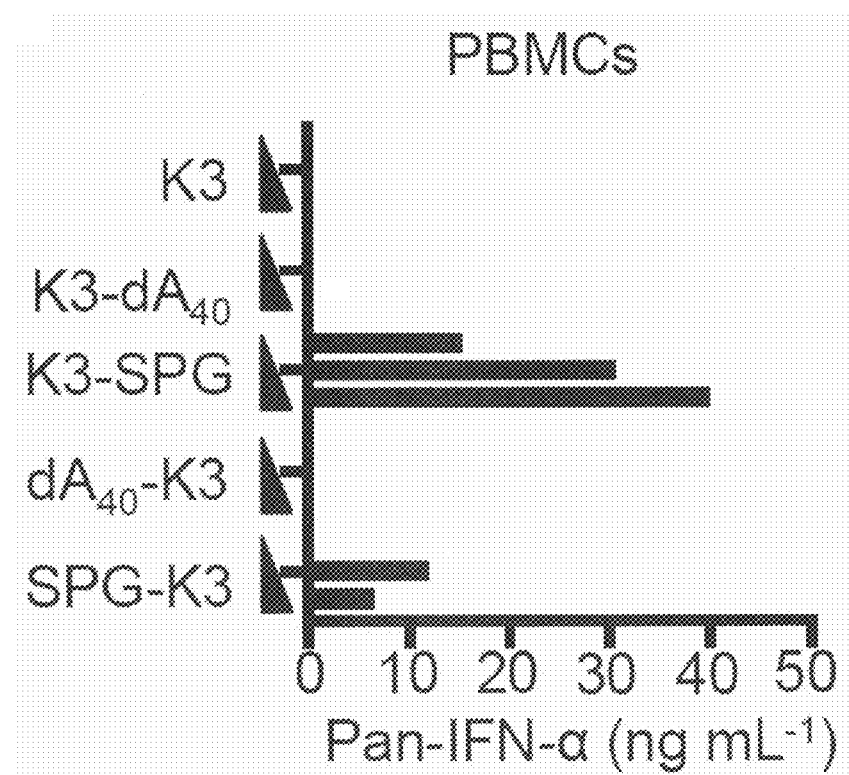
FIG. 2 shows pan-IFN-α production by PBMCs.
Figure 3:
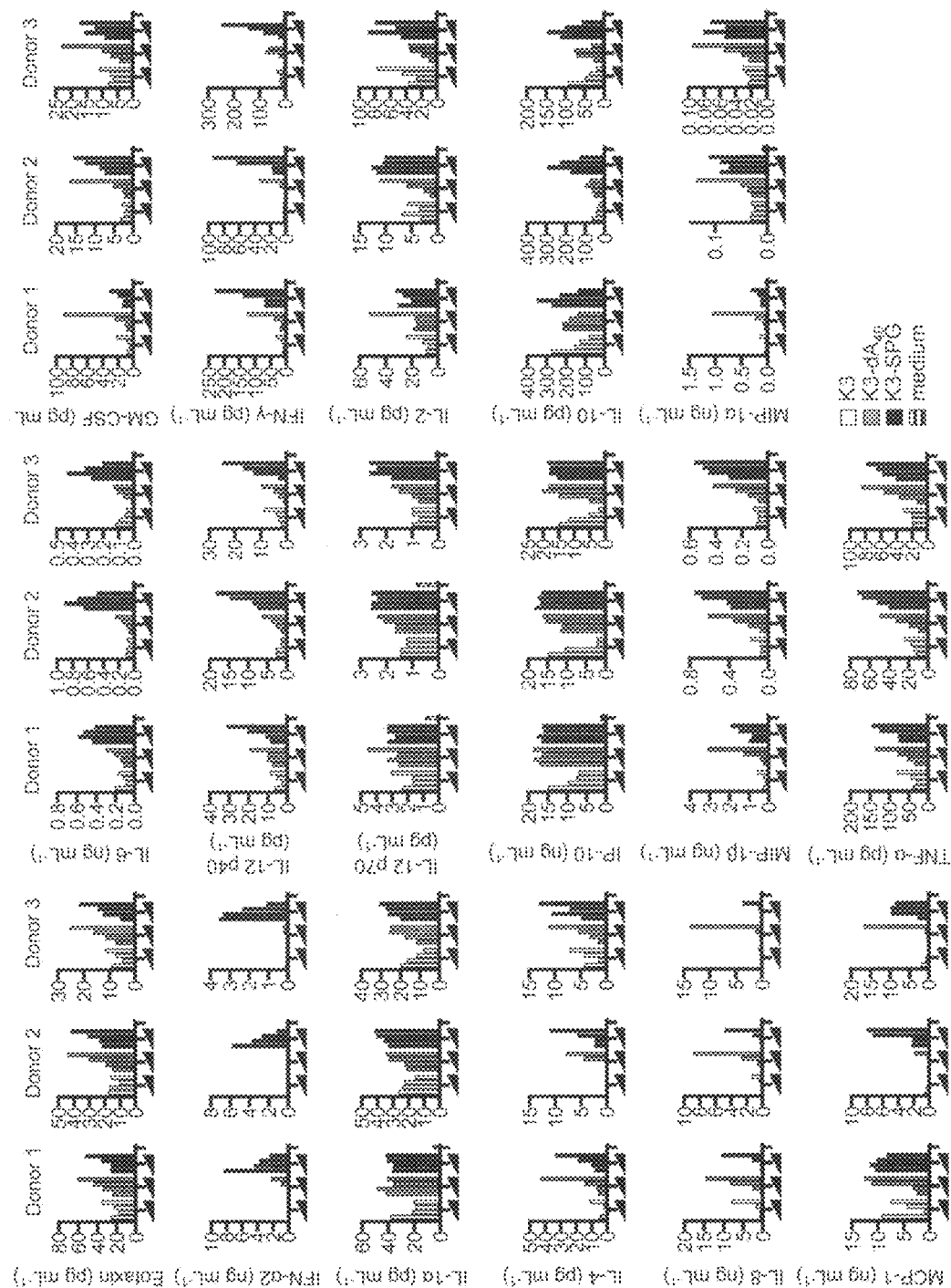
FIG. 3 shows the profile of cytokine produced from human PBMCs on stimulation with K3, K3-dA40 or K3-SPG.

Better complexation efficiency between CpG ODN and SPG requires additional sequences of the PS backbone for poly-dA40 at 5' or 3' ends through denaturing-renaturing procedures as shown in FIG. 1 (Shimada, N., et al., Bioconjugate chemistry 18, 1280-1286 (2007); Minari, J., et al., Bioconjugate chemistry 22, 9-15 (2011)). During optimization of the complex formation by humanized CpG ODN, the present inventors examined the immunostimulatory impacts of the 5'- and 3'-ends of CpG ODN. The 5'-K3-dA40-3', but not 5'-dA40-K3-3', complexed with SPG activated human peripheral blood mononuclear cells (PBMCs) to produce robust amount of IFN-α, although complexation efficiencies were comparable (FIGS. 2 and 3). K3, K3-dA40, and dA40-K3, which are able to activate human PBMCs to produce other cytokines, such as IL-6, failed to produce IFN-α (FIGS. 2 and 3). These results indicate that the 5'-CpG is more desirable than the 3'-CpG as a novel TLR9 agonist.

Qualification and quantitation of K3-SPG was conducted by scanning electron microscopy (SEM) and dynamic light scattering (DLS). K3-SPG had a rod-like structure, consistent with that seen in a previous report (Bae, A. H., et al., Carbohydrate research 339, 251-258 (2004)) (FIG. 4). It appeared to be a soluble monomeric nano-particle with an average diameter of 30 nm, comparable to SPG itself and smaller than D type CpG ODN (D35) (FIG. 5) (Klein, D. C. et al., Ultramicroscopy 110, 689-693 (2010); Costa, L. T., et al., Biochemical and biophysical research communications 313, 1065-1072 (2004)).

Figure 7:
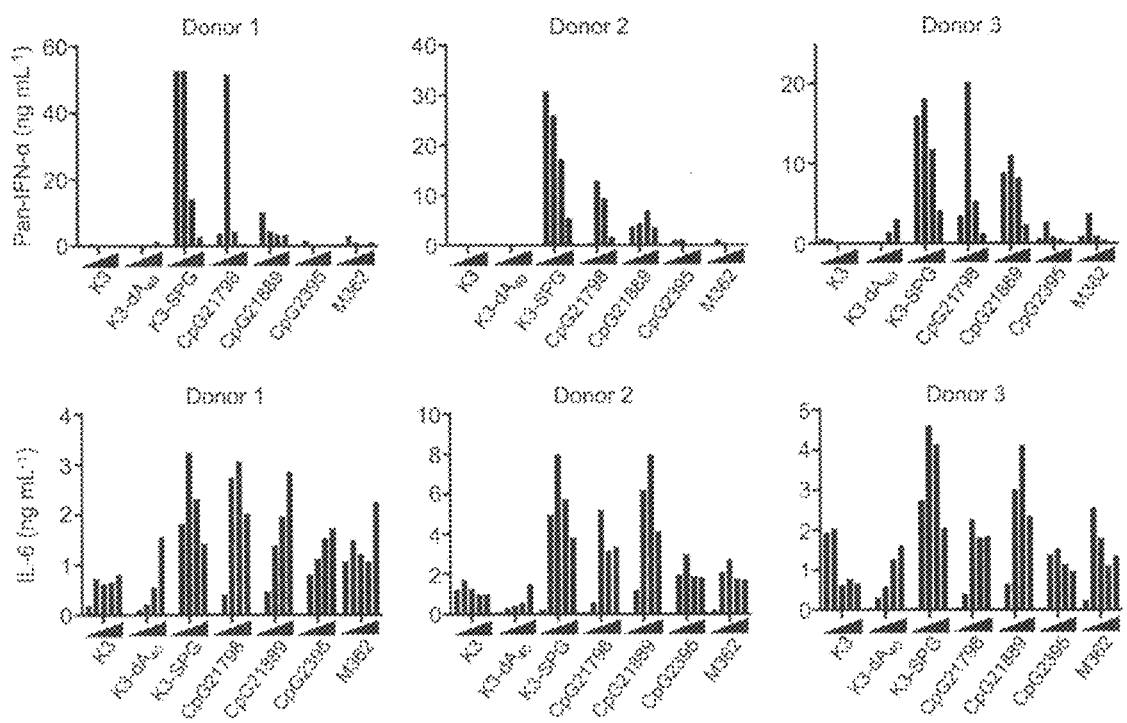
FIG. 7 shows production of pan-IFN-α and IL-6 by human PBMCs, which is induced by stimulation with K3, K3-dA40, K3-SPG, CpG21798 (P type CpG ODN), CpG21889(P), CpG2395(C) or M362(C) (0.74, 2.2, 6.6 or 20 μg/ml).

Given that K3-SPG forms a nano-particle, the immunostimulatory activities of K3-SPG was compared with C, D and P type CpG ODN. PBMCs stimulated with K3-SPG produced larger amount of IFN-α and IFN-γ, and at far lower concentrations than those induced by D35 (FIG. 6), P and C type CpG ODN (FIG. 7). These results suggest that K3-SPG gains a characteristic of D type CpG ODN, without losing that of the K type, because these IFNs are known to be D type-specific cytokines (Krug, A., et al., European journal of immunology 31, 2154-2163 (2001); Verthelyi, D. et al., Journal of immunology 166, 2372-2377 (2001); Gursel, M. et al., Journal of leukocyte biology 71, 813-820 (2002)). To understand the dual functions of K and D type CpG ODN, the present inventors analyzed the intracellular localization of K3-SPG in bone marrow-derived macrophages. K3-SPG was co-localized with not only the endosomes containing K type CpG ODN but also those containing D type CpG ODN (FIGS. 8 and 9) like C type CpG ODN (Guiducci, C., et al., The Journal of experimental medicine 203, 1999-2008 (2006)), suggesting that K3-SPG may transduce endosome-mediated innate immune signaling pathways by K and D type CpG ODN. These results strongly suggest that K3-SPG forms a nano-sized high-order and completely solubilized particle and found that this "all-in-one" K3-SPG displayed a more potent activity than, and different characteristic from, any other CpG ODNs and previously known CpG-SPG complex.

2) K3-SPG is a Prominent Vaccine Adjuvant that Induces Potent CTL Responses to Protein Antigen without Conjugation.

Figure 11:
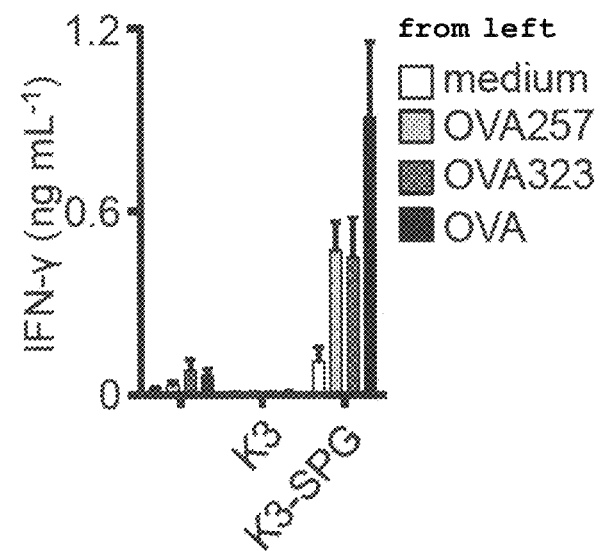
FIG. 11 shows IFNγ production by splenocytes of mice immunized with OVA alone, OVA+K3, or OVA+K3-SPG, which was induced by restimulation with the antigen.
Figure 12:
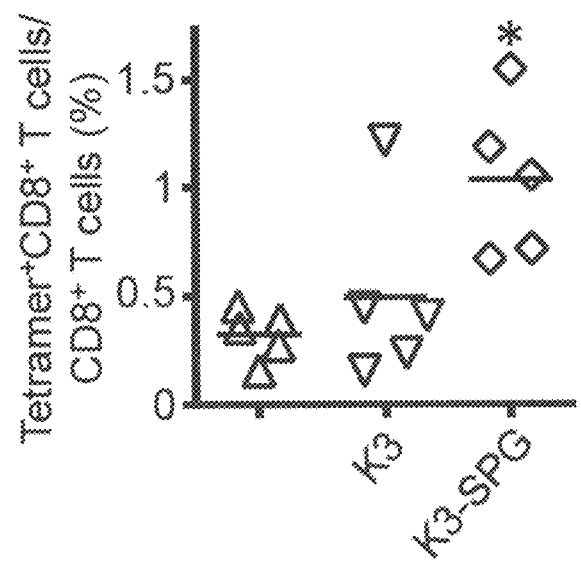
FIG. 12 shows the proportion of OVA-specific CD8 T cells induced by immunization with OVA alone, OVA+K3, or OVA+K3-SPG. *$p<0.05$ (Mann-Whitney U test).
Figure 15:
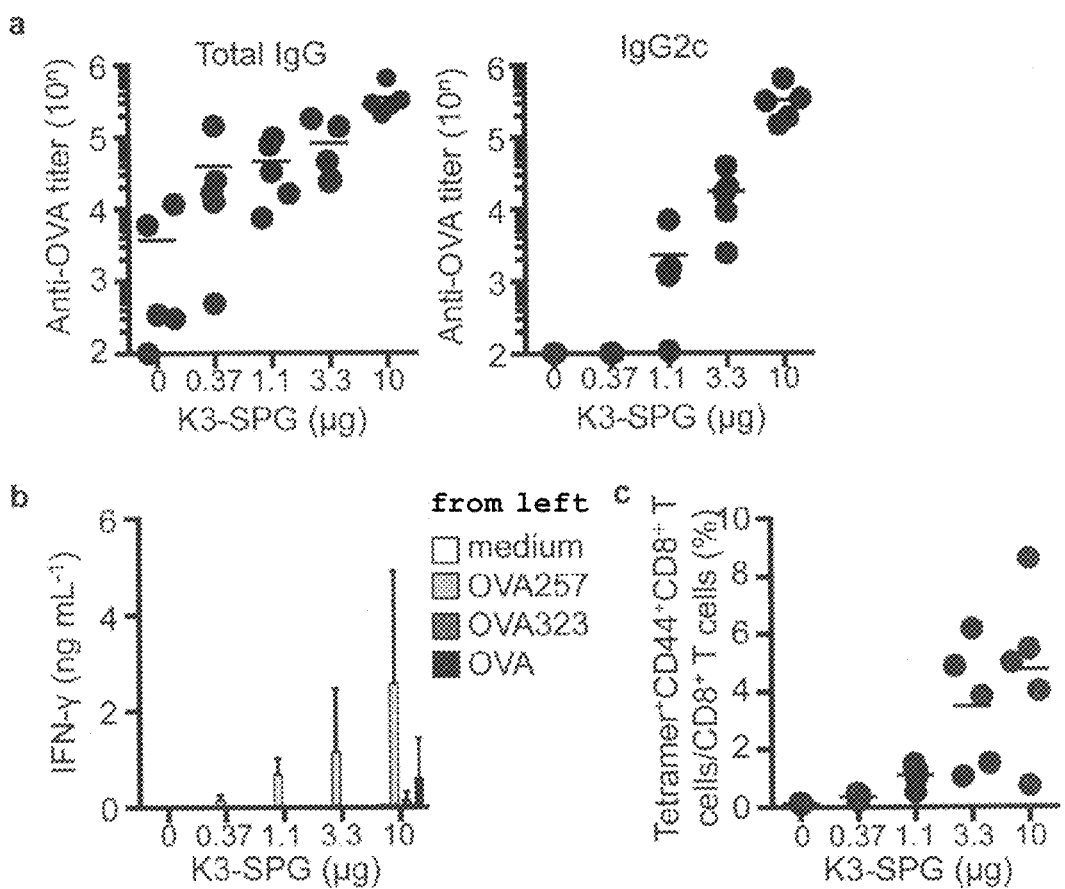
FIG. 15 shows a dose-dependent adjuvant effect of K3-SPG.
Figure 16:
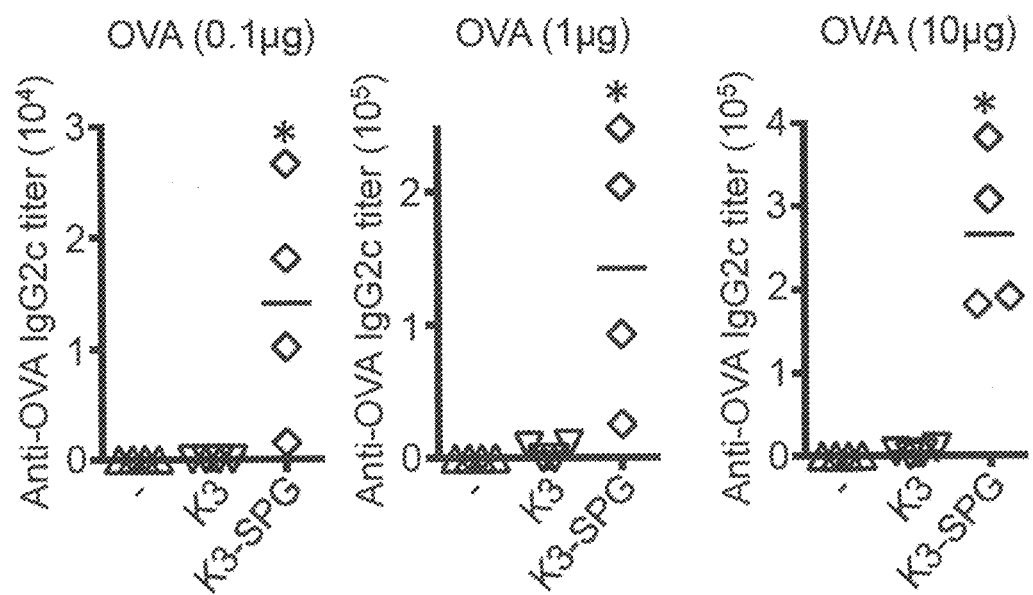
FIG. 16 shows antigen specific serum antibody titers of mice immunized with OVA alone, OVA+K3, or OVA+K3-SPG. The OVA dose at the time of immunization is shown on each graph. *$p<0.05$ (Mann-Whitney U test).
Figure 17:
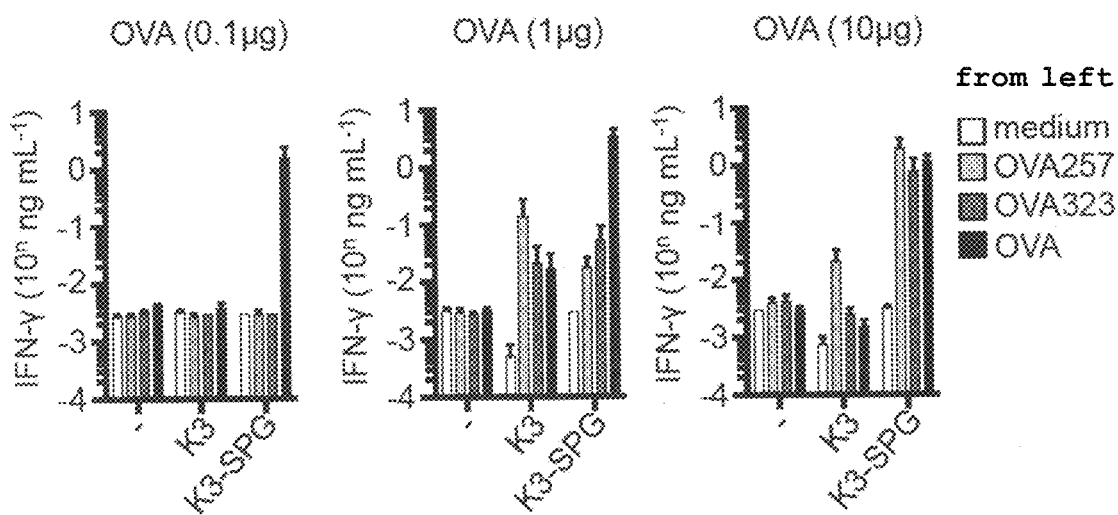
FIG. 17 shows IFNγ production by splenocytes of mice immunized with OVA alone, OVA+K3, or OVA+K3-SPG, which was induced by restimulation with the antigen. The OVA dose at the time of immunization is shown on each graph.

The present inventors compared the adjuvant effects of K3, K3-dA40, and K3-SPG in a murine immunization model. When wild-type mice were immunized with OVA alone, or OVA with each K3-derived adjuvant, K3-SPG induced significantly higher humoral immune responses (FIG. 10), and stronger T cell responses than that induced by K3 (FIG. 11). Of note, tetramer assays revealed a significantly greater number of OVA-specific CD8 T cells (FIG. 12). Very strong in vivo CTL activity against co-administered protein antigens without any covalent conjugation was also observed (FIG. 13). This strong CTL induction by K3-SPG was reproduced by peptide vaccination (FIG. 14), and was dose-dependent (FIG. 15). The antigen-sparing ability of K3-SPG was so potent that comparable antibody and CD4 T cell responses were achieved using one-hundredth the amount of OVA antigen (FIGS. 16 and 17). These results clearly indicate that K3-SPG is a prominent adjuvant than K3 alone.

3) SPG is a Soluble Dectin-1 Ligand, but is not a Dectin-1 Agonist.

Figure 21:
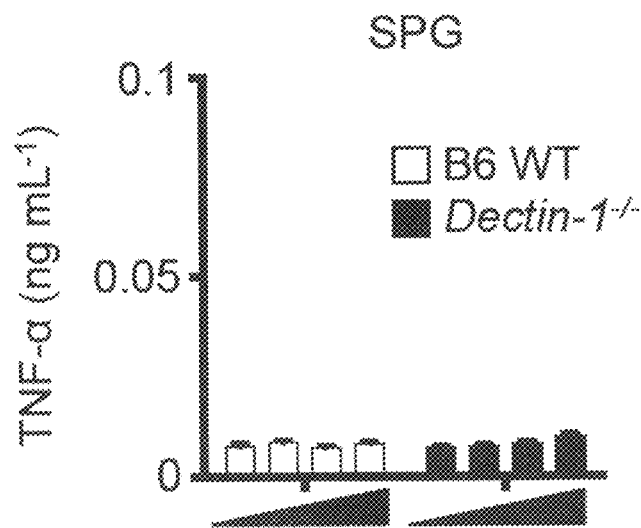
FIG. 21 shows TNF-α production by splenocytes of C57BL/6J mouse or Dectin-1 deficient mouse, which was induced by SPG stimulation.
Figure 22:
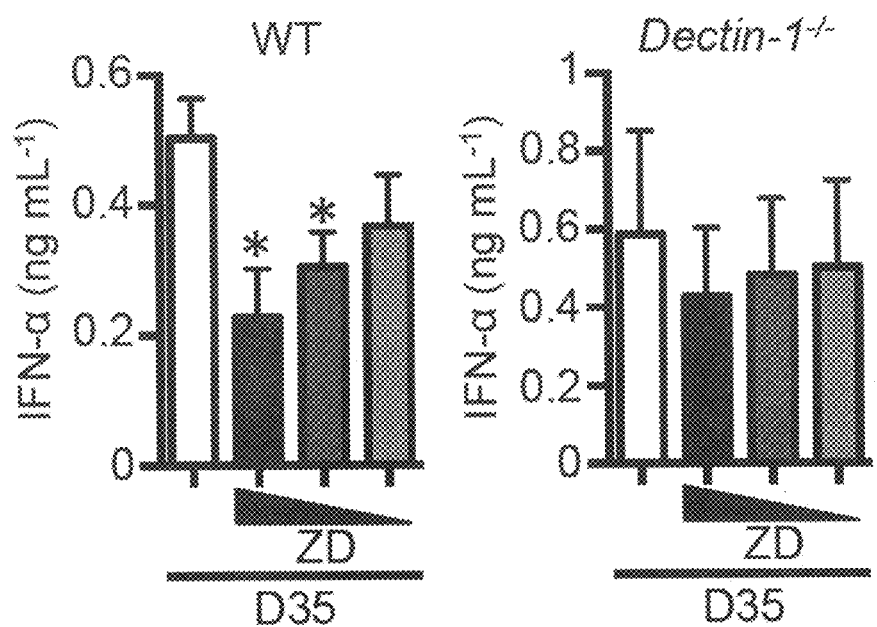
FIG. 22 shows the effect of Zymosan Depleted on IFN-α production by splenocytes of C57BL/6J mouse or Dectin-1 deficient mouse, which was induced by CpG ODN stimulation. *$p<0.05$ (t-test).
Figure 23:
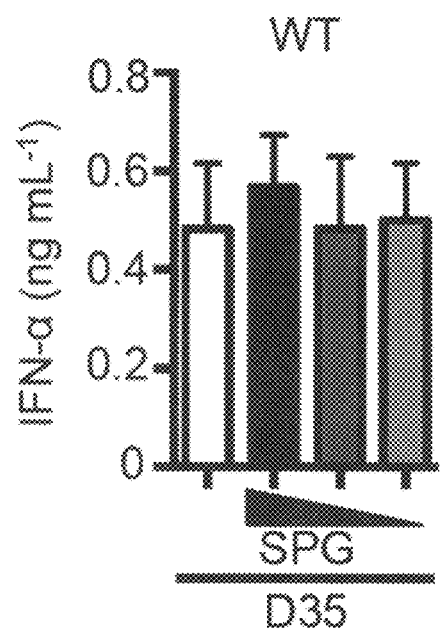
FIG. 23 shows the effect of SPG on IFN-α production by splenocytes of C57BL/6J mouse, which was induced by CpG ODN stimulation.

The role of Dectin-1 in cellular uptake of, and following activation by, SPG and K3-SPG was examined, as Dectin-1 has been shown to be a receptor for β-glucans such as Zymosan (Herre, J., et al., Blood 104, 4038-4045 (2004)). Using flow cytometry, it was found that HEK293 cells expressing Dectin-1 but not Dectin-2 or a control vector, increased the uptake of SPG or K3-SPG in vitro regardless of ODN presence (FIGS. 18 and 19). It has recently been reported that the soluble form of β-glucan does not activate Dectin-1 signaling (Goodridge, H. S., et al., Nature 472, 471-475 (2011)). Additionally, Dectin-1 signaling inhibits TLR9-mediated cytokine production through suppressor of cytokine signaling protein 1 (SOCS1) induction (Eberle, M. E. & Dalpke, A. H., Journal of immunology 188, 5644-5654 (2012)). Therefore, the agonistic activity of SPG was examined. When spleen cells were stimulated with Zymosan-Depleted but not SPG, dose- and Dectin-1-dependent TNF-α and other cytokine productions were observed (FIG. 20) (FIG. 21). Cytokine productions by Zymosan and Curdlan were Dectin-1-independent. Zymosan-Depleted inhibited CpG ODN-induced IFN-α, with this inhibition relieved by Dectin-1 deficiency (FIG. 22). In contrast, SPG did not inhibit CpG ODN-induced IFN-α production (FIG. 23). These results indicate that SPG is a ligand but not an agonist of Dectin-1; therefore SPG does not interfere with TLR9-mediated IFN-α production.

4) Adjuvant Effects of K3-SPG are Dependent on TLR9 and Partially Dependent on Dectin-1.

Figure 24:
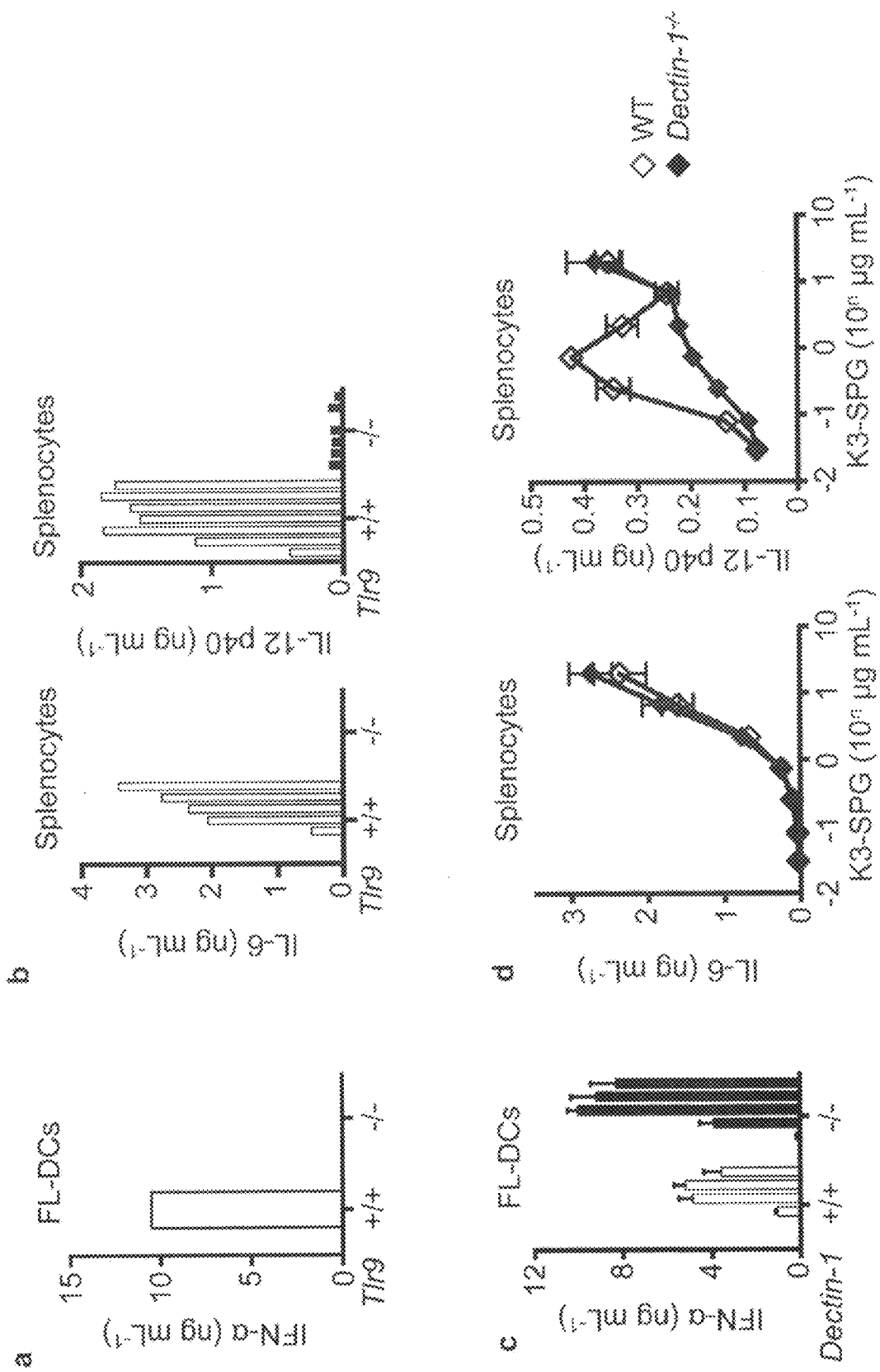
FIG. 24 shows that cytokine production induced by K3-SPG depends on TLR9. a) IFN-α production by FL-DCs, b) IL-6 and IL-12 p40 production by splenocytes, c) IFN-α production by FL-DCs, d) IL-6 and IL-12 p40 production by splenocytes.
Figure 25:
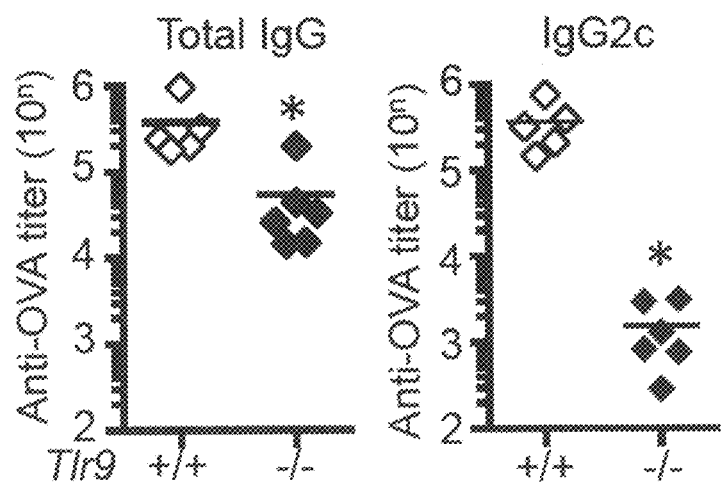
FIG. 25 shows antigen specific serum antibody titers of Tlr9+/+ or Tlr9−/− mice immunized with OVA+K3-SPG. *$p<0.05$ (Mann-Whitney U test).
Figure 26:
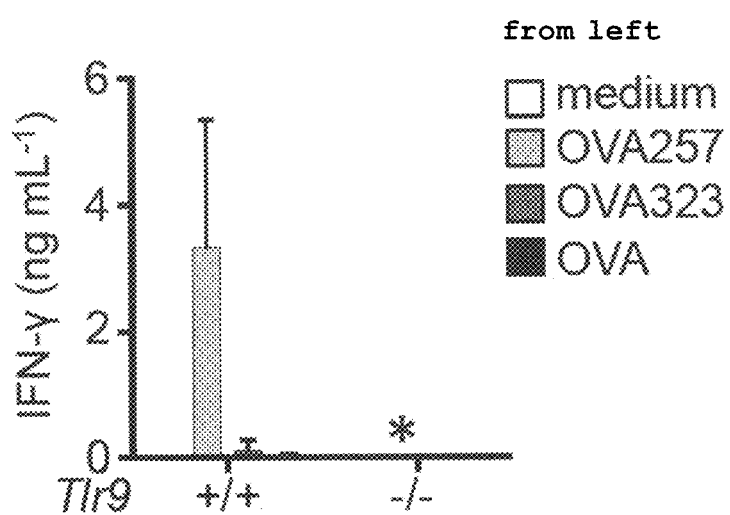
FIG. 26 shows IFN-γ production by splenocytes of Tlr9+/+ or Tlr9−/− mouse immunized with OVA+K3-SPG, which is induced by restimulation with the antigen. *$p<0.05$ (Mann-Whitney U test).
Figure 27:
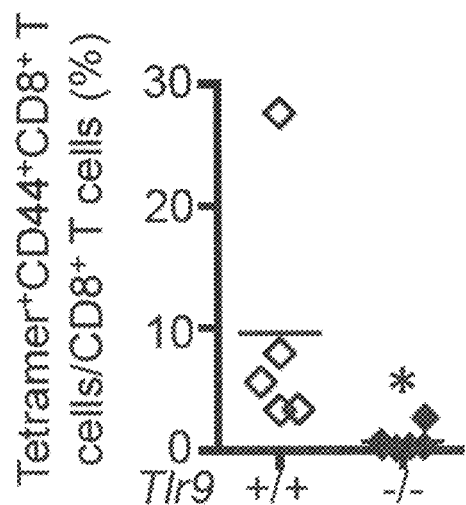
FIG. 27 shows the proportion of OVA-specific CD8 T cells induced by immunization of Tlr9+/+ or Tlr9−/− mouse with OVA+K3-SPG. *$p<0.05$ (Mann-Whitney U test).
Figure 28:
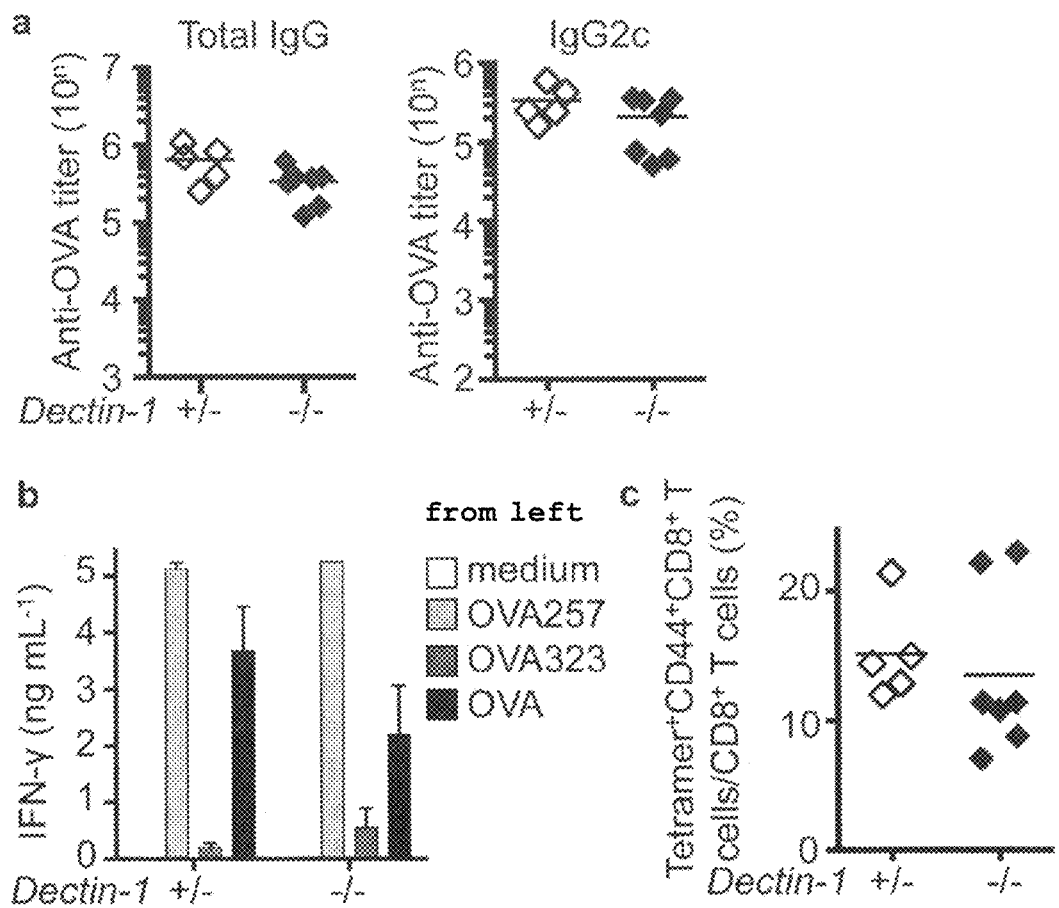
FIG. 28 shows that the adjuvant effect of K3-SPG does not depend on Dectin-1. a) Antigen specific antibody titer in the serum. b) IFN-γ production by splenocyte due to antigen restimulation. c) Proportion of antigen specific CD8 T cells induced in vivo.
Figure 29:
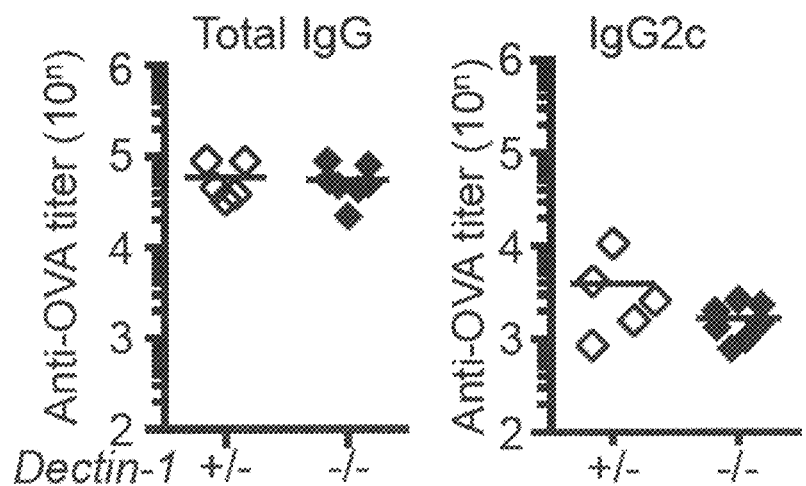
FIG. 29 shows antigen specific serum antibody titers of Dectin-1+/− or Dectin-1−/− mice immunized with OVA+K3-SPG.
Figure 30:
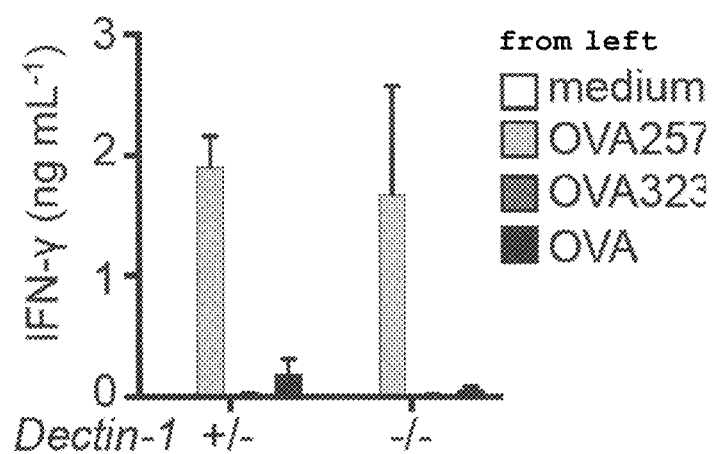
FIG. 30 shows IFNγ production by splenocytes of Dectin-1+/− or Dectin-1−/− mice immunized with OVA+K3-SPG, which was induced by restimulation with the antigen.
Figure 31:
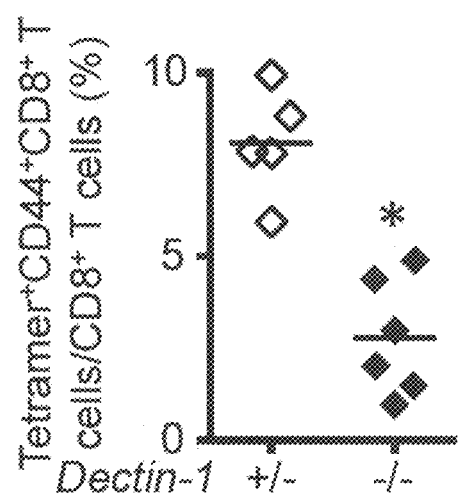
FIG. 31 shows the proportion of OVA-specific CD8 T cells induced by immunization of Dectin-1+/− or Dectin-1−/− mouse with OVA+K3-SPG. *p<0.05 (Mann-Whitney U test).

Since K3-SPG is a complex of CpG ODN and β-glucan, the role of TLR9 (Hemmi, H., et al., Nature 408, 740-745 (2000)) and Dectin-1 (Saijo, S., et al., Nature immunology 8, 39-46 (2007)) was examined using receptor knockout mice. When splenocytes and Flt3 ligand-induced bone marrow-derived DCs (FL-DCs) from Tlr9-deficient and Dectin-1-deficient mice were stimulated with K3-SPG, cytokine production was completely dependent on TLR9 but not Dectin-1 (FIG. 24). Consistent with in vitro results, immunization into Tlr9-deficient mice with K3-SPG plus OVA resulted in diminished humoral and T cell responses (FIGS. 25-27). Dectin-1-deficient mice showed comparable immune responses with wild-type mice when the mice were immunized with OVA plus 10 μg of K3-SPG (FIG. 28). When Dectin-1-deficient mice were immunized with OVA plus 1 μg of K3-SPG, mice exhibited a reduced CD8 T cell response according to the tetramer assays (FIG. 31), with no significant changes in antibody and cytokine production from T cells (FIGS. 29 and 30). These results suggest that the adjuvant effect of K3-SPG is dependent on TLR9 signaling. Although SPG and K3-SPG do not stimulate Dectin-1 signaling, the effect of K3-SPG is still partially dependent on Dectin-1 in vivo.

5) MARCO$^+$, but not Siglec-1$^+$ Macrophages in Draining Lymph Nodes Dominantly Capture K3-SPG with Antigen.

Given that K3-SPG provides potent adjuvant effects in vivo through immunization with a simple antigen mixture, it was hypothesized that cells which capture both antigen and K3-SPG should play a critical role in mediating adjuvant effects. To examine in vivo distribution of fluorescent-labeled OVA and K3-SPG, fluorescence microscope and two-photon microscope were used. After an injection at the base of the tail, both antigen and adjuvant reached the surface of draining inguinal lymph nodes (iLNs) within 1 h (FIGS. 32, 33 and 35). After 24 h, some K3-SPG had moved to the CD3e$^+$ T cell area and co-localized with DQ-OVA. Those cells that contained both K3-SPG and DQ-OVA in the T cell area of the iLN were CD11c$^+$ DCs.

Interestingly, the majority of fluorescence signals remained on the surface of the iLN (FIG. 32), prompting the inventors to focus on two types of macrophages known to be distributed on the LN surface, Siglec-1 (also called CD169 or MOMA-1)$^+$ macrophages (also known as subcapsular sinus macrophages) and MARCO$^+$ macrophages (Martinez-Pomares, L. & Gordon, S., Trends in immunology 33, 66-70 (2012)). Histological analysis using conventional fluorescence microscopy did not suitably reveal the entire iLN surface; moreover, these macrophages were difficult to be isolated for flow cytometric analysis (Aoshi, T., et al., European journal of immunology 39, 417-425 (2009); Gray, E. E. & Cyster, J. G., Journal of innate immunity 4, 424-436 (2012)). Hence, two-photon microscopy imaging analysis was used to clarify the distribution of antigen and K3-SPG ex vivo. After the injection of anti-MARCO and anti-Siglec-1 antibodies, specific macrophages were visualized. When the iLN surface was monitored by two-photon microscopy at 1 h post-injection, OVA and K3-SPG were co-localized with MARCO$^+$ but not Siglec-1$^+$ macrophages (FIGS. 33 and 35). Previous reports suggest the immune complex and inactivated influenza virus are captured by Siglec-1$^+$ macrophages to induce humoral immune responses (Gonzalez, S. F., et al., Nature immunology 11, 427-434 (2010); Suzuki, K. et al., The Journal of experimental medicine 206, 1485-1493 (2009)). The distribution pattern perfectly matched that for MARCO$^+$ macrophages in the iLNs, and did not co-localize with Siglec-1$^+$ macrophages as confirmed by Volocity's co-localization analysis (FIGS. 34 and 36). In contrast, K3 was more diffusely distributed between MARCO$^+$ and Siglec-1$^+$ areas compared with K3-SPG (FIGS. 35 and 36). Additionally, both Tlr9-deficient and Dectin-1-deficient mice showed comparable localization of K3-SPG. To determine the contribution of these macrophages towards the adjuvant effects of K3-SPG, different recovery kinetics of macrophages and DCs following an injection of clodronate liposome into the base of the tail was examined. After the injection, macrophages were completely depleted by day 2. These cells did not recover for at least one week, while DCs were mostly recovered by day 5, as previously reported (Aoshi, T., et al., Immunity 29, 476-486 (2008)). When both macrophages and DCs were depleted, immune responses were significantly suppressed (FIG. 37; Clo-d2). Only macrophages, but not DCs, were depleted and the immune responses were comparable with those in untreated mice (FIG. 37; Clo-d5). This would suggest that although both OVA and K3-SPG were mainly captured by MARCO$^+$ macrophages in the LNs after injection, the macrophages induced adaptive immune responses. In other words, the adjuvant effect of K3-SPG was largely dependent on the DC population.

6) K3-SPG Targets and Strongly Activates the Antigen-Bearing DC Population In Vivo.

The present inventor's findings suggest that although a large portion of nano-particulate K3-SPG was taken up by MARCO$^+$ macrophages in the iLNs after injection, the adjuvant effects appear to be controlled by DCs. Antigen and adjuvant uptake by the DC population in iLNs was focused. At 24 h post-injection, the uptake of antigen and adjuvants by the DC population was analyzed by flow cytometry. The frequency of CpG-positives in three DC subsets (pDCs, CD8α$^+$ DCs, and CD8α$^-$ DCs) was significantly increased after the K3-SPG injection than with K3. In contrast, the frequency of OVA-positive DCs was comparable after K3 and K3-SPG injections. When focused on both antigen- and adjuvant-positive DCs, there was substantial increase for K3-SPG over K3. Both pDCs and CD8α$^+$ DCs in the iLNs were strongly activated by K3-SPG but not by K3 24 h post-injection, and this was totally dependent on TLR9 (FIG. 38). These results indicate that pDCs and CD8α$^+$ DCs preferentially capture nano-particulate K3-SPG rather than non-particulate K3 for maturation, and to exert adjuvant effects.

7) K3-SPG is a Potent Adjuvant for Influenza Vaccine in Murine and Non-Human Primate Models.

Figure 43:
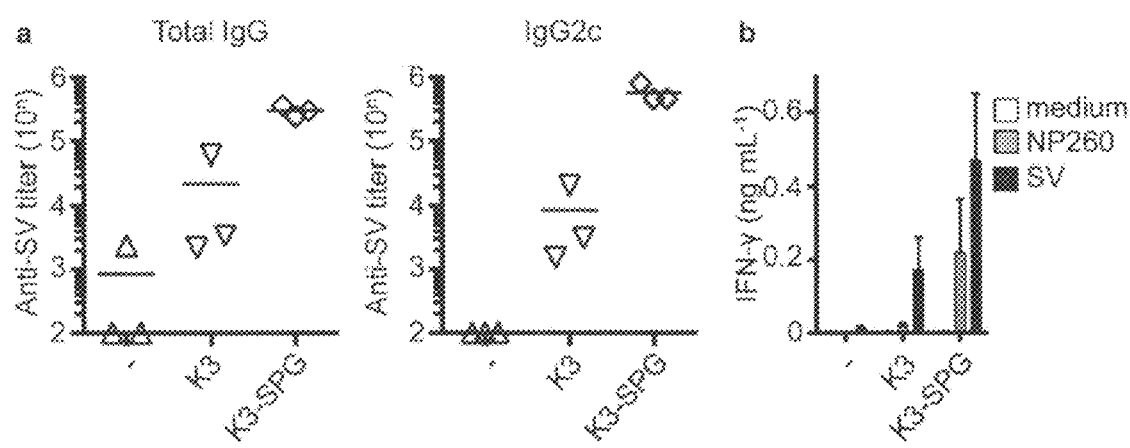
FIG. 43 shows comparison of vaccine adjuvant effect between K3 and K3-SPG.

The adjuvant effect of K3-SPG was examined by using more clinical relevant influenza vaccination models in both mice and non-human primates. When mice were immunized with ether-treated hemagglutinin antigen-enriched virion-free split vaccine (SV) plus the indicated adjuvant, K3-SPG demonstrated superior adjuvant effects than K3 when antibody responses and T cell responses were compared (FIG. 43). More importantly, a SV plus K3-SPG immunization resulted in a 100-fold greater antibody response, even compared with vaccination with a whole (virion) inactivated vaccine (WIV) (0.2 µg/mouse) (FIG. 39), which contains viral RNA as a built in adjuvant (Koyama, S., et al., Science translational medicine 2, 25ra24 (2010)). The mice immunized with SV (0.1 µg/mouse) and K3-SPG exhibited less body weight loss than WIV-immunized mice (FIG. 40). Strikingly, K3-SPG conferred 100% protection against lethal PR8 virus challenge, at the dose of which only 10% of WIV vaccinated mice survived (FIG. 40). These results strongly support the notion that K3-SPG works as a potent adjuvant for protein or protein-based vaccines in a murine model, prompting the inventors to extend this finding to a non-human primate model using cynomolgus monkey. Each group of three cynomolgus monkeys was immunized with SV plus K3 or K3-SPG at days 0 and 14. Serum antibody titers were then monitored for 8 weeks. The SV plus K3-SPG induced significantly higher antibody titer at 2 weeks post-immunization, and titer levels remained high for at least another 6 weeks (FIG. 41). At 2 years (110 weeks) after the immunization, the K3-SPG group had significantly higher antibody titers than in the K3 group (FIGS. 42 and 43). Taken together, these results suggested that K3-SPG is a prominent vaccine adjuvant in a non-human primate model.

8) Investigation of Inflammation Response Inducing Ability of K3-LNT and K3-SPG Complexes Using Human PBMCs Using human PBMCs (Lonza, Cat#CC-2702, Lot#0000396517), an ability of K3 (K3-dA30, K3-dA35, K3-dA40) alone, K3-LNT complexes (K3-dA30-LNT, K3-dA35-LNT, K3-dA40-LNT) and K3-SPG complex (K3-dA40-LNT) to induce production of pan-IFN-α (hIFNa) and IL-6 (hIL-6) was evaluated.

Figure 44:
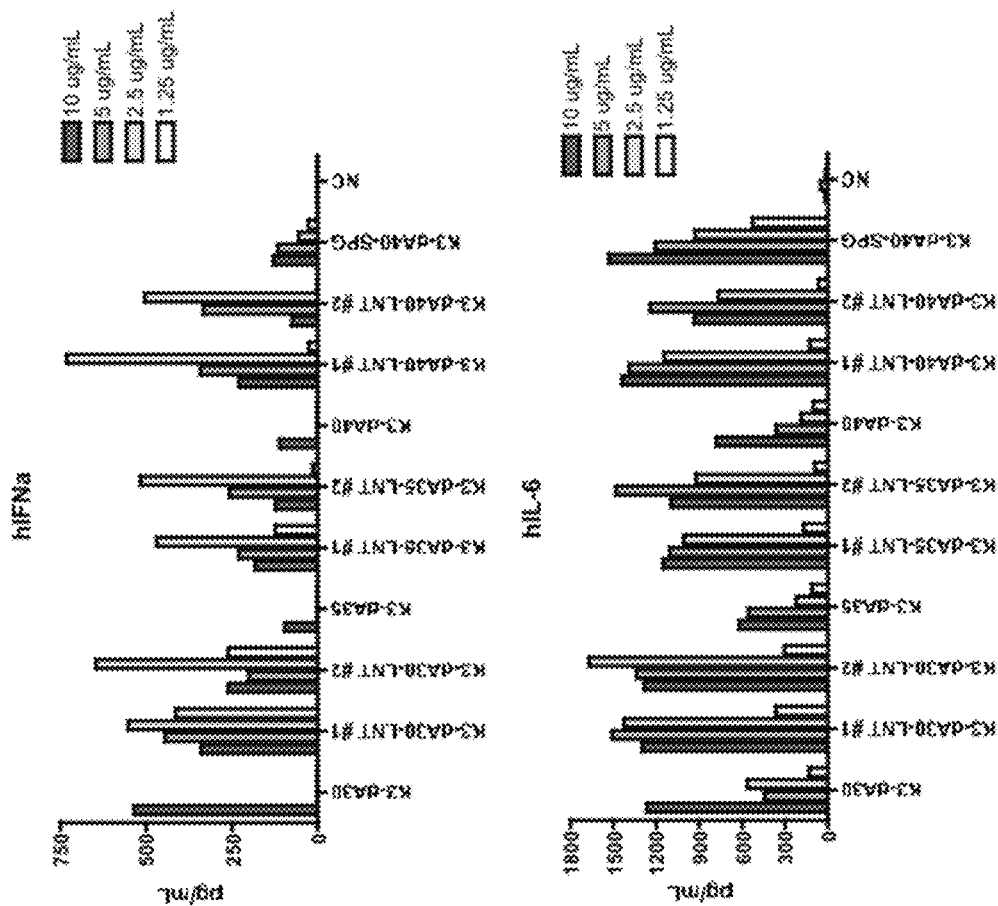
FIG. 44 shows pan-IFN-α production and IL-6 production by K3, K3-LNT or K3-SPG.

The results are shown in FIG. 44. When stimulated at a low dose, the production of pan-IFN-α and IL-6 was higher with K3-SPG which is a complex of K3 and SPG, and K3-LNT which is a complex of K3 and LNT, as compared to K3 alone. In addition, inflammatory cytokine producibility which is induced by K3-LNTs having different dA tail length (dA30, dA35, dA40) was suggested to be possibly almost equivalent. Furthermore, when inflammatory cytokine producibility of K3-SPG and K3-LNT was compared, pan-IFN-α production inducibility of K3-LNT was suggested to be possibly higher than that of K3-SPG. On the other hand, K3-SPG and K3-LNT were found to be equivalent in the IL-6 production.

Figure 45:
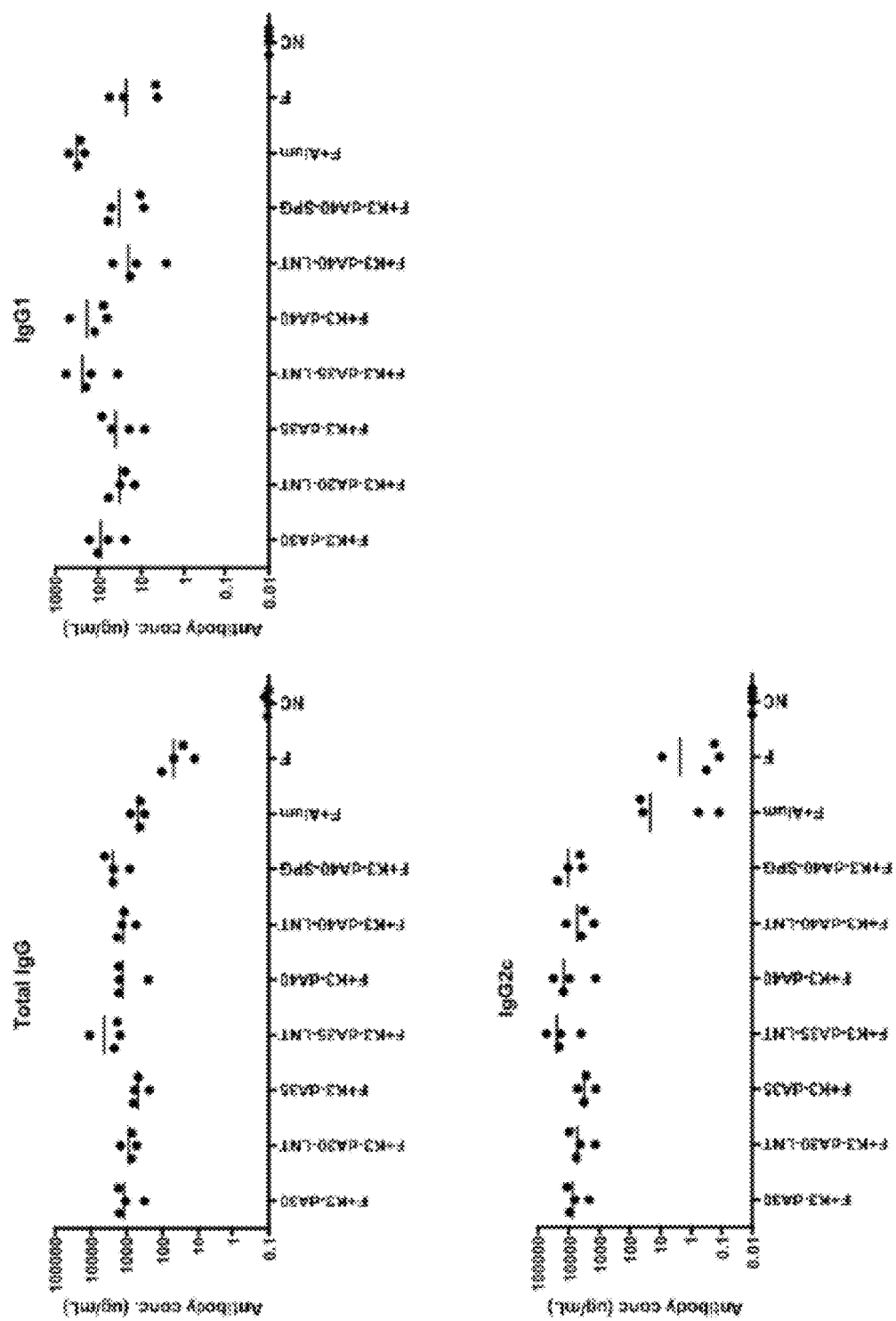
FIG. 45 shows RSV F antigen specific IgG antibody titers in the serum of mice inoculated with K3-, K3-LNT- or K3-SPG-added RSV F subunit vaccine.

9) RSV F Antigen Specific IgG Antibody Titer in the Sera of Mice Inoculated with RSV F Subunit Vaccine Added with K3-LNT and K3-SPG Complex 7-week-old C57BL/6 mice were immunized twice at the tail base with RSV F antigen (0.5 µg) and various adjuvants (10 µg) (K3 alone (K3-dA30, K3-dA35, K3-dA40), K3-LNT complex (K3-dA30-LNT, K3-dA35-LNT, K3-dA40-LNT) and K3-SPG complex (K3-dA40-SPG), alum phosphate), per mouse, at 2-week intervals. At one week after the final immunization, peripheral blood was recovered and the serum was prepared, which were used as evaluation samples. The titer of the antibody which binds to the RSV F vaccine antigen in the serum was measured using the ELISA method. As shown in FIG. 45, RSV F antigen-specific total IgG induction was enhanced by the addition of adjuvant as compared to RSV F antigen alone inoculation group (F), which suggests that the adjuvant effect of K3 alone (F+K3-dA30, F+K3-dA35, F+K3-dA40), K3-LNT (F+K3-dA30-LNT, F+K3-dA35-LNT, F+K3-dA40-LNT) and K3-SPG complex (F+K3-dA40-SPG) and alum phosphate (F+Alum) may be equivalent. In the mouse group inoculated with alum phosphate (F+Alum), which is a Th2 adjuvant, it was found that the IgG1 subclass induction ability was higher than the RSV F antigen along inoculation group. On the other hand, the results showed that the immunization group inoculated with K3 alone (F+K3-dA30, F+K3-dA35, F+K3-dA40), K3-LNT (F+K3-dA30-LNT, F+K3-dA35-LNT, F+K3-dA40-LNT), K3-SPG (F+K3-dA40-SPG) was higher in IgG2c subclass antibody than with alum phosphate (F+Alum), which suggests that the K3-LNT complex may be a Th1 adjuvant like K3-SPG.

10) RSV F Antigen-Specific Cytokine Production Ability in Mouse Inoculated with RSV F Subunit Vaccine Added with K3-LNT and K3-SPG Complex 7-week-old C57BL/6 mice were immunized twice at the tail base with RSV F antigen (0.5 μg) and various adjuvants (10 μg) (K3 alone (K3-dA30, K3-dA35, K3-dA40), K3-LNT (K3-dA30-LNT, K3-dA35-LNT, K3-dA40-LNT) and K3-SPG complex (K3-dA40-SPG), alum phosphate), per mouse, at 2-week intervals. At one week after the final immunization, the spleen was recovered, and splenocytes were prepared. The splenocytes seeded in a 96 well culture plate were stimulated with each of MHC class I restricted epitope peptide, MHC class II restricted epitope peptide, and vaccine antigen protein of the RSV F antigen, and cultured for 24 hr or 48 hr. The RSV F antigen-specific cytokine production ability was evaluated by the cytokine ELISA method and using the culture supernatant as a sample. In this investigation, three kinds of cytokines (IFN-g which is a Th1 cytokine, IL-2 produced from activated T cells, and IL-13 which is a Th2 cytokine) were evaluated.

Figure 46:
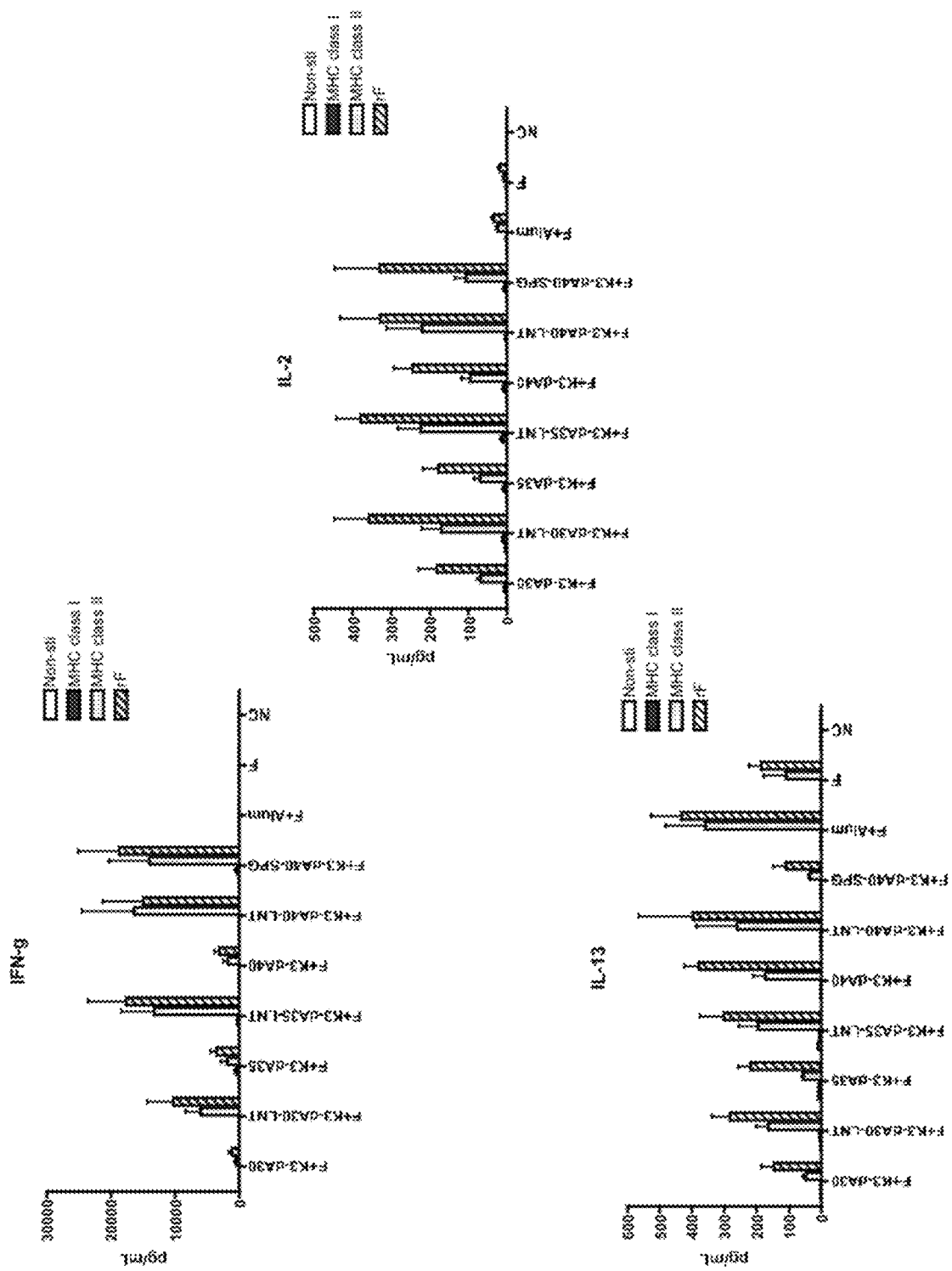
FIG. 46 shows cytokine production specifically induced by RSV F antigen stimulation in mice inoculated with K3- or K3-LNT- or K3-SPG-added RSV F subunit vaccine.

As a result, as shown in FIG. 46, it was suggested that enhancing effects on RSV F antigen-specific induction of IFN-g production and IL-2 production may be equivalent in K3-LNT (F+K3-dA30-LNT, F+K3-dA35-LNT, F+K3-dA40-LNT) and K3-SPG (F+K3-dA40-SPG). In the alum phosphate adjuvant (Th2 adjuvant) inoculation group (F+Alum), IFN-g production was below the detection limitation level by any stimulation. On the other hand, the IL-13 production enhancing effect was high in the alum phosphate (Th2 adjuvant) inoculation group and low in the K3-SPG (Th1 adjuvant) inoculation group. Interestingly, in the K3-LNT inoculation group (F+K3-dA30-LNT, F+K3-dA 35-LNT, F+K3-dA 40-LNT), the enhancing effect on IL-13 production was high as compared to the same Th1 adjuvant (K3-SPG) inoculation group (F+K3-dA40-SPG). Therefrom it was suggested that K3-LNT complex has a Th2 response enhancing ability in addition to the high Th1 response enhancing effect possessed by K3-SPG.

11) Protective Effect Against RSV Infection in Cotton Rats Inoculated with RSV F Subunit Vaccine Added with K3-LNT and K3-SPG 6- to 7-week-old cotton rats were immunized twice to the tail base with RSV F antigen (1 μg) and various adjuvants (10 μg) (K3-LNT (K3-dA35-LNT, K3-dA40-LNT) and K3-SPG complex (K3-dA40-SPG), alum phosphate), per rat, at 2-week intervals. At two weeks after the final immunization, the cotton rats were challenged with RSV serotype A (Long strain) by transnasal inoculation, and the intrapulmonary viral amount was measured 3 days later. The Synagis (palivizumab) administration group was intramuscularly administered with Synagis (2.5 mg/kg) one day before challenge infection, and the infection protective ability was evaluated in the same manner as above. Blood samples were collected from the jugular vein of the rats under anesthesia immediately before challenge infection and the neutralizing antibody titer was investigated using the obtained serum.

Figure 47:
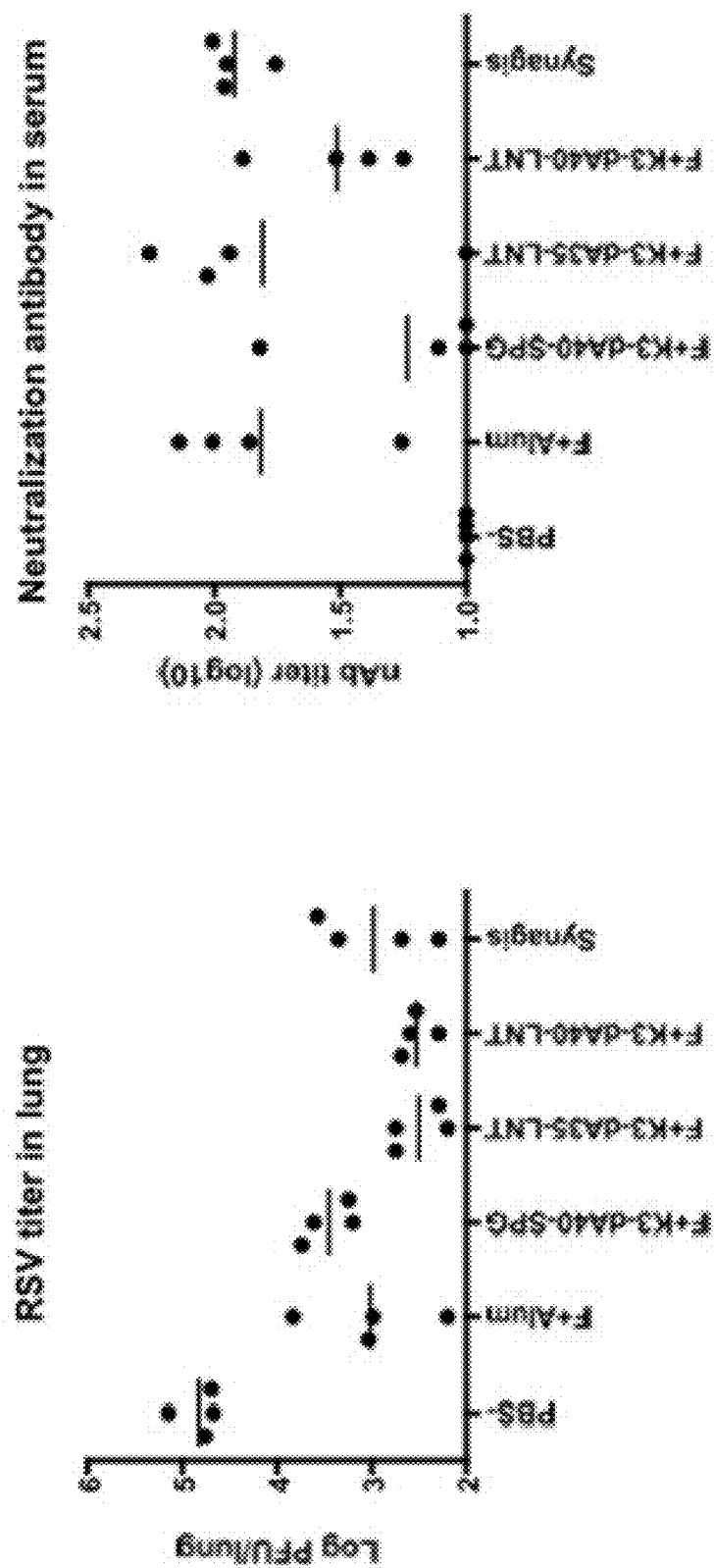
FIG. 47 shows RSV infection protective effect in cotton rats inoculated with K3- or K3-LNT- or K3-SPG-added RSV F subunit vaccine.

The results of the intrapulmonary viral amount are shown in the left of FIG. 47, and the results of the neutralizing antibody titer are shown in the right thereof. The results of the intrapulmonary viral amount reveal that a viral amount of about $10^5$ pfu/lung is observed in the PBS-administration group, whereas it was suppressed to about 100 times lower viral amount (mean) in the group administered with alum phosphate-added RSV F vaccine (F+Alum). On the other hand, activity to induce protection from infection was observed also in the K3-SPG-added vaccine administration group (F+K3-dA40-SPG). The K3-LNT-added vaccine group (F+K3-dA35-LNT, F+K3-dA40-LNT) showed the best protective effect from infection, thus suggesting the possibility of being a novel vaccine adjuvant candidate, which contributes to a high infection defense ability, as compared to alum phosphate and K3-SPG.

As for the neutralizing antibody inducing ability, neutralizing activity in blood equivalent to Synagis was found in the alum phosphate-added vaccine administration group (F+Alum). On the other hand, since neutralizing antibody was scarcely induced in 3 out of 4 rats in the K3-SPG-added vaccine administration group (F+K3-dA40-SPG), the infection protective effect to which K3-SPG contributes was considered to stem from a neutralizing antibody-independent mechanism. In addition, since a high neutralizing antibody was found in the K3-LNT administration group (F+K3-dA35-LNT, F+K3-dA40-LNT), as compared to K3-SPG, it was suggested that K3-LNT adjuvant may have a property different from that of K3-SPG, for example, a Th2 response enhancing ability.

INDUSTRIAL APPLICABILITY

The present invention provides an oligodeoxynucleotide having a superior immunostimulating activity and a complex containing same. Particularly, the complex of the present invention concurrently has an immunostimulating activity unique to K type CpG ODN and an immunostimulating activity unique to D type CpG ODN. Furthermore, K3-SPG and K3-LNT have a strong vaccine adjuvant activity, and immunization with K3-SPG or K3-LNT together with an antigen stimulates both the antigen-specific humoral immunity and cellular immunity. Therefore, the complex of the present invention is useful as an immunostimulating agent or vaccine adjuvant in the medicament field.

This application is based on a patent application No. 2013-196206 filed in Japan (filing date: Sep. 20, 2013), the contents of which are incorporated in full herein.

The invention claimed is:

1. A method for the treatment of a cancer in a warm-blooded animal, comprising administering to the warm-blooded animal a pharmacologically effective amount of a complex comprising:
   (i) an oligodeoxynucleotide comprising humanized K type CpG oligodeoxynucleotide consisting of the nucleotide sequence shown by SEQ ID NO: 1 and poly deoxyadenylate of 20-60 nucleotide length, wherein the poly deoxyadenylate is bound at the 3'-end of the humanized K type CpG oligodeoxynucleotide, and wherein all of the phosphodiester bonds are substituted by phosphorothioate bonds; and
   (ii) lentinan.

2. The method according to claim 1, wherein an antigen is further administered to the warm-blooded animal, and the antigen is therapeutic for the cancer.

3. The method according to claim 1, wherein the complex has a triple helix structure.

4. The method according to claim 1, wherein the complex has an activity to activate B cells to produce IL-6, and an activity to activate dendritic cells to produce IFN-α.

5. The method according to claim 1, wherein the warm-blooded animal is human.

6. A method of inducing a protective immune reaction in a warm-blooded animal in need of the treatment or prophylaxis of a cancer, comprising administering to the warm-blooded animal the following (a) and (b):
   (a) a pharmacologically effective amount of a complex comprising:
      (i) an oligodeoxynucleotide comprising humanized K type CpG oligodeoxynucleotide consisting of the nucleotide sequence shown by SEQ ID NO: 1 and poly deoxyadenylate of 20-60 nucleotide length, wherein the poly deoxyadenylate is bound at the 3'-end of the humanized K type CpG oligodeoxynucleotide, and wherein all of the phosphodiester bonds are substituted by phosphorothioate bonds; and (ii) lentinan; and (b) an antigen that is therapeutic or prophylactic for the cancer.

7. The method according to claim 6, wherein the complex has a triple helix structure.

8. The method according to claim 6, wherein the complex has an activity to activate B cells to produce IL-6, and an activity to activate dendritic cells to produce IFN-α.

9. The method according to claim 6, wherein the warm-blooded animal is human.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 1
atcgactctc gagcgttctc                                                    20

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 2
atcgactctc gagcgttctc aaaaaaaaaa aaaaaaaaaa aaaaaaaaaa aaaaaaaaaa         60

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 3
aaaaaaaaaa aaaaaaaaaa aaaaaaaaaa aaaaaaaaaa atcgactctc gagcgttctc         60

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ggtgcatcga tgcagggggg                                                    20

<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
tcgtcgacga tcggcgcgcg ccg                                                23

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 6
tcgtcgacga tcggcgcgcg ccg                                                23

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
tcgtcgtttt cggcgcgcgc cg                                                 22

```
<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 8
tcgtcgtcgt tcgaacgacg ttgat                                               25

<210> SEQ ID NO 9
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 9
atcgactctc gagcgttctc aaaaaaaaaa aaaaaaaaaa                               40

<210> SEQ ID NO 10
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 10
atcgactctc gagcgttctc aaaaaaaaaa aaaaaaaaaa aaaaa                         45

<210> SEQ ID NO 11
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 11
atcgactctc gagcgttctc aaaaaaaaaa aaaaaaaaaa aaaaaaaaaa                    50

<210> SEQ ID NO 12
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 12
atcgactctc gagcgttctc aaaaaaaaaa aaaaaaaaaa aaaaaaaaaa aaaaa              55
```